(12) United States Patent
Galabova et al.

(10) Patent No.: US 10,004,791 B2
(45) Date of Patent: Jun. 26, 2018

(54) PEPTIDE VACCINES AGAINST PCSK9

(71) Applicant: AFFIRIS AG, Vienna (AT)

(72) Inventors: Gergana Galabova, Vienna (AT); Guenther Staffler, Vienna (AT); Sylvia Brunner, Vienna (AT); Gabriele Winsauer, Vienna (AT); Andreas Mairhofer, Vienna (AT); Claudia Juno, Vienna (AT)

(73) Assignee: AFFIRIS AG, Vienna (AT)

( * ) Notice: Subject to any disclaimer, the term of this patent is extended or adjusted under 35 U.S.C. 154(b) by 0 days. days.

(21) Appl. No.: 15/122,316

(22) PCT Filed: Feb. 23, 2015

(86) PCT No.: PCT/EP2015/053725
§ 371 (c)(1),
(2) Date: Aug. 29, 2016

(87) PCT Pub. No.: WO2015/128287
PCT Pub. Date: Sep. 3, 2015

(65) Prior Publication Data
US 2017/0065689 A1 Mar. 9, 2017

(30) Foreign Application Priority Data
Feb. 28, 2014 (EP) .................... 14157221

(51) Int. Cl.
*A61K 39/00* (2006.01)
*A61K 47/48* (2006.01)
*C07K 16/40* (2006.01)
*C12N 9/64* (2006.01)
*A61K 38/00* (2006.01)

(52) U.S. Cl.
CPC .......... *A61K 39/0005* (2013.01); *C07K 16/40* (2013.01); *C12N 9/6454* (2013.01); *C12Y 304/21061* (2013.01); *A61K 38/00* (2013.01); *A61K 2039/55505* (2013.01); *A61K 2039/55516* (2013.01); *A61K 2039/57* (2013.01); *A61K 2039/627* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | |
|---|---|---|
| 2011/0052621 A1 | 3/2011 | Champion et al. |
| 2013/0273081 A1 | 10/2013 | Monaci et al. |
| 2015/0071951 A1 | 3/2015 | Brunner et al. |
| 2015/0098957 A1 | 4/2015 | Champion et al. |

FOREIGN PATENT DOCUMENTS

| | | |
|---|---|---|
| WO | 2011/027257 A2 | 3/2011 |
| WO | 2011/117401 A1 | 9/2011 |
| WO | 2013/037889 A2 | 3/2013 |
| WO | 2013/148284 A1 | 10/2013 |

OTHER PUBLICATIONS

International Search Report dated Jun. 19, 2015 in PCT/EP2015/053725 filed Feb. 23, 2015.
Y. Luo, et al., "Function and distribution of circulating human PCSK9 expressed extrahepatically in transgenic mice," Journal of Lipid Research, 2009, vol. 50, pp. 1581-1588, XP 55126035A.
M. Amar, et al., "Anti-PCSK9 VLP Immunization Reduces Cholesterol Levels in Mice and Non-human Primates," Core 2. Epidemiology and Prevention of CV Disease: Physiology, Pharmacology and Lifestyle, 2014, 1 page.
C. L. Brazolot Millan, et al., "CpG DNA can induce strong Th1 humoral and cell-mediated immune responses against hepatitis B surface antigen in young mice," Proceedings of the National Academy of Sciences of the United States of America, Dec. 1998, vol. 95, pp. 15553-15558.
H. L. Davis, et al., "CpG DNA is a Potent Enhancer of Specific Immunity in Mice Immunized with Recombinant Hepatitis B Surface Antigen," The Journal of Immunology, 1998, vol. 160, 8 pages.
P. Garcia, et al., "Nucleotide sequence and expression of the pneumococcal autolysin gene from its own promoter in *Escherichia coli*," Gene, 1986, vol. 43, pp. 265-272.
M. J. McCluskie, et al., "Cutting Edge: CpG DNA is a Potent Enhancer of Systemic and Mucosal Immune Responses Against Hepatitis B Surface Antigen with Intranasal Administration to Mice," The Journal of Immunology, 1998, vol. 161, 5 pages.
Y. Sato, et al., "Immunostimulatory DNA Sequences Necessary for Effective Intradermal Gene Immunization," Science, Jul. 19, 1996, vol. 273, pp. 352-354.
D. Steinberg, "An interpretive history of the cholesterol controversy: part II: the early evidence linking hypercholesterolemia to coronary disease in humans," Journal of Lipid Research, 2005, vol. 46, 13 pages.
D. Steinberg, "An interpretive history of the cholesterol controversy: part V: The discovery of the statins and the end of the controversy," Journal of Lipid Research, 2006, vol. 47, pp. 1339-1351.
X. Sun, et al., "Preprotein Convertase Subtilisin/Kexin Type 9 Deficiency Reduces Melanoma Metastasis in Liver," Neoplasia, Dec. 2012, vol. 14, No. 12, 14 pages.
M. Singh, et al., "Advances in vaccine adjuvants," Nature Biotechnology, Nov. 1999, vol. 17, pp. 1075-1081.
D. T. O'Hagan, et al., "Recent Advances in the Discovery and Delivery of Vaccine Adjuvants," Nature Reviews Drug Discovery, Sep. 2003, vol. 2, pp. 727-735.
G. T. Hermanson, "Bioconjugate techniques," 2013, ISBN: 976-0-12-382239-0.

(Continued)

Primary Examiner — Elly-Gerald Stoica
(74) Attorney, Agent, or Firm — Oblon, McClelland, Maier & Neustadt, L.L.P.

(57) ABSTRACT

The present invention relates to a vaccine capable to induce production of antibodies directed to PCSK9 in vivo.

17 Claims, 6 Drawing Sheets

(56) References Cited

OTHER PUBLICATIONS

Ribi, et al., "Immunology and Immunopharmacology of Bacterial Endotoxins," 1986, pp. 407-419 ISBN: 978-1-4613-2253-5.
European Search Report dated Jul. 10, 2014 in EP 14157221.4 Filed Feb. 28, 2014.
Written Opinion of the International Preliminary Examining Authority dated Jan. 25, 2016 in PCT/EP2015/053725 filed Feb. 23, 2015.

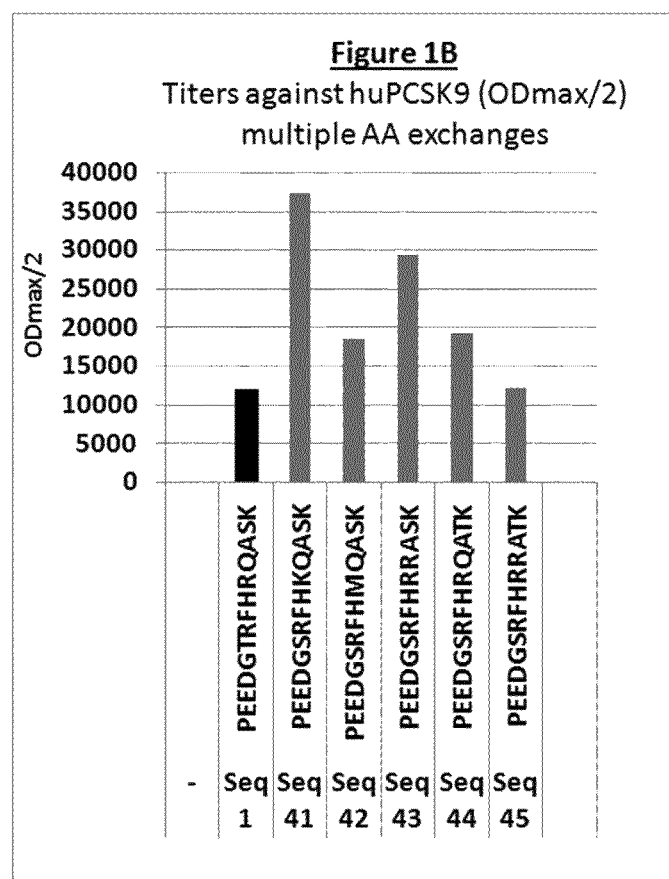

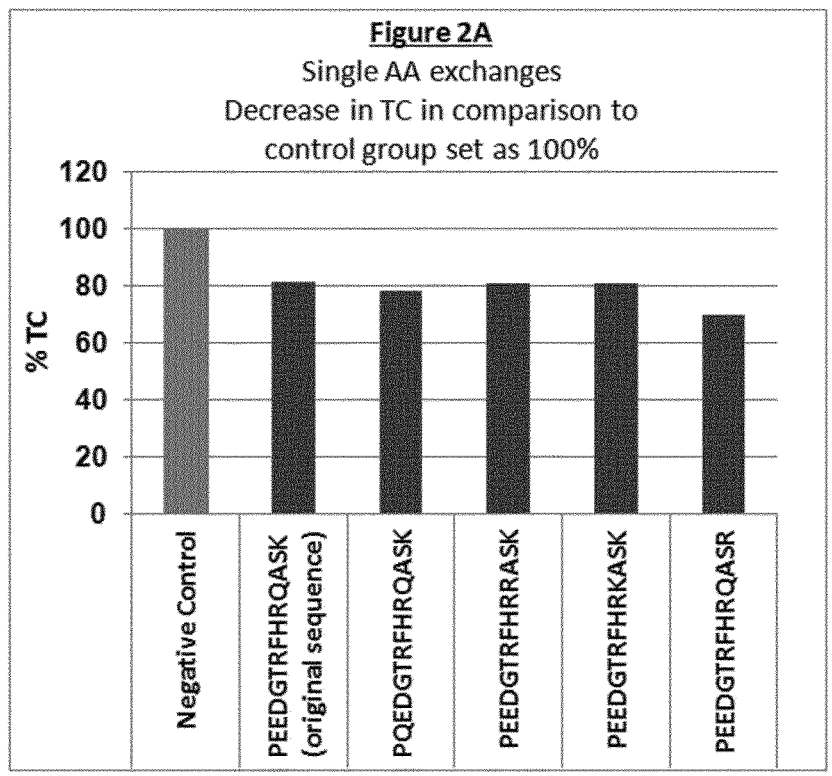
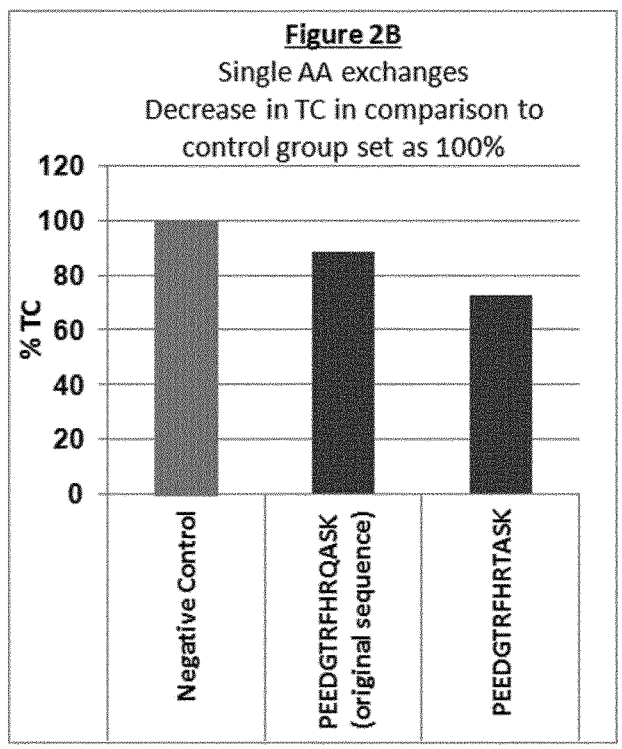

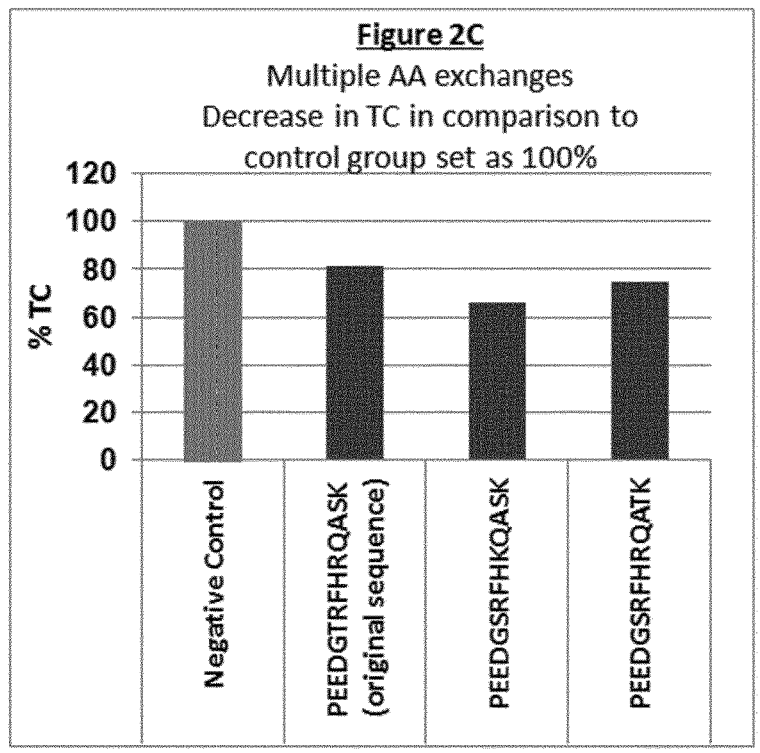
Figure 3
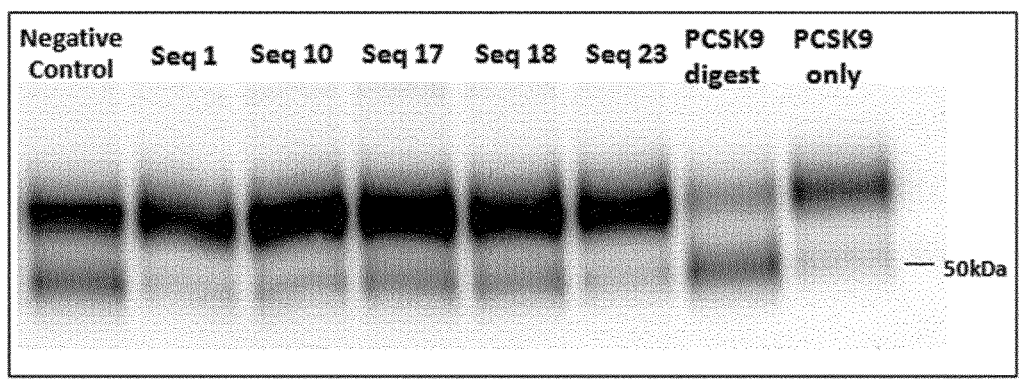

SEQUENCE LISTING

```
<160> NUMBER OF SEQ ID NOS: 47

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Glu Glu Asp Gly Thr Arg Phe His Arg Gln Ala Ser Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Glu Glu Asp Gly Thr Arg Phe His Arg Gln Ala Ser Lys
1               5                   10
```

```
<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Ala Glu Asp Gly Thr Arg Phe His Arg Gln Ala Ser Lys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Glu Glu Asp Gly Thr Arg Phe Ala Arg Gln Ala Ser Lys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Glu Glu Asp Gly Thr Arg Phe His Ala Gln Ala Ser Lys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Glu Glu Asp Gly Thr Arg Phe His Arg Ala Ala Ser Lys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Glu Glu Asp Gly Thr Arg Phe His Arg Gln Ala Ala Lys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 8

Pro Glu Glu Asp Gly Thr Arg Phe His Arg Gln Ala Ser Ala
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Glu Glu Asp Gly Thr Arg Phe His Arg Gln Ala Ser Lys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Gln Glu Asp Gly Thr Arg Phe His Arg Gln Ala Ser Lys
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Lys Glu Asp Gly Thr Arg Phe His Arg Gln Ala Ser Lys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Glu Glu Asp Gly Ser Arg Phe His Arg Gln Ala Ser Lys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Glu Glu Asp Gly Thr Arg Phe His Gln Gln Ala Ser Lys
1               5                   10

<210> SEQ ID NO 14
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Glu Glu Asp Gly Thr Arg Phe His Lys Gln Ala Ser Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Glu Glu Asp Gly Thr Arg Phe His Met Gln Ala Ser Lys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Glu Glu Asp Gly Thr Arg Phe His Arg Glu Ala Ser Lys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Glu Glu Asp Gly Thr Arg Phe His Arg Arg Ala Ser Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Glu Glu Asp Gly Thr Arg Phe His Arg Lys Ala Ser Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Glu Glu Asp Gly Thr Arg Phe His Arg Gln Ser Ser Lys
```

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Glu Glu Asp Gly Thr Arg Phe His Arg Gln Ala Thr Lys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Glu Glu Asp Gly Thr Arg Phe His Arg Gln Ala Asn Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Glu Glu Asp Gly Thr Arg Phe His Arg Gln Ala Leu Lys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Glu Glu Asp Gly Thr Arg Phe His Arg Gln Ala Ser Arg
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Glu Glu Asp Gly Thr Arg Phe His Arg Gln Ala Ser Leu
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 25

Lys Glu Glu Asp Gly Thr Arg Phe His Arg Gln Ala Ser Lys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Glu Trp Asp Gly Thr Arg Phe His Arg Gln Ala Ser Lys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Glu Glu Asp Lys Thr Arg Phe His Arg Gln Ala Ser Lys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Glu Glu Asp Gly Thr Gly Phe His Arg Gln Ala Ser Lys
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Pro Glu Glu Asp Gly Thr Arg Phe Ser Arg Gln Ala Ser Lys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Glu Glu Asp Gly Thr Arg Phe Thr Arg Gln Ala Ser Lys
1               5                   10

<210> SEQ ID NO 31

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Glu Glu Asp Gly Thr Arg Phe Val Arg Gln Ala Ser Lys
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Glu Glu Asp Gly Thr Arg Phe Gly Arg Gln Ala Ser Lys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Glu Glu Asp Gly Thr Arg Phe Met Arg Gln Ala Ser Lys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Glu Glu Asp Gly Thr Arg Phe His Pro Gln Ala Ser Lys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Glu Glu Asp Gly Thr Arg Phe His Ser Gln Ala Ser Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

Pro Glu Glu Asp Gly Thr Arg Phe His Arg Thr Ala Ser Lys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Glu Glu Asp Gly Thr Arg Phe His Arg Gln Thr Ser Lys
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Pro Glu Glu Asp Gly Thr Arg Phe His Arg Gln Ala Ser Ser
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Glu Glu Asp Gly Thr Arg Phe His Arg Gln Ala Ser Thr
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Glu Glu Asp Gly Thr Arg Phe His Arg Gln Ala Ser Val
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Glu Glu Asp Gly Ser Arg Phe His Lys Gln Ala Ser Lys
1               5                   10

<210> SEQ ID NO 42
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 42

Pro Glu Glu Asp Gly Ser Arg Phe His Met Gln Ala Ser Lys
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Glu Glu Asp Gly Ser Arg Phe His Arg Arg Ala Ser Lys
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Glu Glu Asp Gly Ser Arg Phe His Arg Gln Ala Thr Lys
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Glu Glu Asp Gly Ser Arg Phe His Arg Arg Ala Thr Lys
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Thr, Ala or Pro
<220> FEATURE:
<221> NAME/KEY: MOD_RES
<222> LOCATION: (2)..(2)
<223> OTHER INFORMATION: Gln or Asp
<220> FEATURE:
<221> NAME/KEY: MOD_RES
<222> LOCATION: (6)..(6)
<223> OTHER INFORMATION: Thr or Ser
<220> FEATURE:
<221> NAME/KEY: MOD_RES
<222> LOCATION: (9)..(9)
<223> OTHER INFORMATION: His, Ala or Ser
<220> FEATURE:
<221> NAME/KEY: MOD_RES
<222> LOCATION: (10)..(10)
<223> OTHER INFORMATION: Arg, Ala, Gln, Lys, Met, Pro or Ser
<220> FEATURE:

```
<221> NAME/KEY: MOD_RES
<222> LOCATION: (11)..(11)
<223> OTHER INFORMATION: Gln, Ala, Glu, Lys, Thr or Arg
<220> FEATURE:
<221> NAME/KEY: MOD_RES
<222> LOCATION: (12)..(12)
<223> OTHER INFORMATION: Ala, Ser or Thr
<220> FEATURE:
<221> NAME/KEY: MOD_RES
<222> LOCATION: (13)..(13)
<223> OTHER INFORMATION: Ser, Ala or Asn
<220> FEATURE:
<221> NAME/KEY: MOD_RES
<222> LOCATION: (14)..(14)
<223> OTHER INFORMATION: Lys, Ala, Arg, Leu, Ser, Thr or Val
<220> FEATURE:
<223> OTHER INFORMATION: See specification as filed for detailed
      description of substitutions and preferred embodiments

<400> SEQUENCE: 46

Xaa Xaa Glu Asp Gly Xaa Arg Phe Xaa Xaa Xaa Xaa Xaa Xaa
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 47

His His His His His His
1               5
```

PEPTIDE VACCINES AGAINST PCSK9

SEQUENCE LISTING

The instant application contains a Sequence Listing which has been submitted electronically in ASCII format and is hereby incorporated by reference in its entirety. Said ASCII copy, created on Oct. 28, 2016, is named 474922US99PCT_SL.txt and is 13,499 bytes in size.

The present invention relates to immunogenic peptides capable to induce the formation of antibodies directed to Proprotein Convertase Subtilisin/Kexin Type 9 (PCSK9).

Vascular disorders such as hypercholesterolemia, atherosclerosis, coronary heart disease and stoke are one of the main cause of death worldwide and elevated levels of Low Density Lipoprotein cholesterol (LDLc) are playing key role in their pathogenesis. Thus, LDLc management is a very important element for a successful treatment of dyslipidemia and atherosclerosis.

The discovery of PCSK9 in 2003 and its identification as the third factor, among LDLR and ApoB-100, involved in the development of the Autosomal Dominant Hypercholesterolemia (ADH), brought a new inside into the mechanism of the ADH disease development. Additionally, genetics studies in humans confirmed the connection between LDLc levels, PCSK9 and the onset of coronary heart disease. Link between PCSK9 and elevated LDLc has been also observed in different animal models.

PCSK9 is mainly expressed in the liver, intestine and kidney and is also found secreted in the blood stream. It directly interacts with the low density lipoprotein (LDL) receptor (LDLR), and the formed complex is subsequently internalized. By binding LDLR, PCSK9 promotes the receptor degradation and results in plasma LDLc elevation. "Gain of function mutations" (GOF) in the PCSK9 gene enhance its interaction with the LDLR, leading to markedly higher LDLc levels, subsequent hypercholesterolemia and predisposition to atherosclerosis. Whereas, PCSK9 "Loss of function mutations" (LOF) mutations are linked to reduced risk for coronary heart disease (CHD). Interestingly, two cases of healthy women having loss of functional PCSK9 and very low LDLc (~14 mg/dL) highlighted PCSK9 as non-essential and as promising target for lowering LDLc levels in the blood stream.

PCSK9 over-expression in wild type mice reduces significantly the hepatic LDLR protein, despite the stable mRNA levels, leading to increased circulating LDLc. In comparison, overexpression of PCSK9 in LDLR −/− mice, does not influence the levels of LDLc, confirming the dependence of PCSK9 on LDLR for playing a role in the LDL catabolism. And as expected, PCSK9−/− mice showed a 2.8 fold increase in the levels of LDLR and reduction of LDLc compared to wild type animals. Finally, PCSK9 secretion in the circulation was abrogated, upon inactivation of PCSK9 in the liver tissue, confirming the liver as the major organ responsible for the PCSK9 secretion.

Thus, PCSK9 plays a crucial role in LDL catabolism though the direct actions on LDLR. Inhibition of PCSK9 turns to be beneficial for the LDLc levels. Therefore, anti-PCSK9 therapies are promising approach in terms of beneficial modulation of LDLc levels.

PCSK9, also known as neural apoptosis-regulated convertase 1 (NARC-1), is a secreted proteinase K-like subtilase and member of the mammalian proprotein convertase (PC) family. It is synthesized as a ~72 kDa proprotein and in order to be functional, the precursor (pro-PCSK9) is processed for autocatalysis. This results in the formation of a product (aa31-152) that binds non-covalently tight in 1:1 complex formation with the PCSK9 fragment (aa153-692) in this mature form (~60-63 kDa) PCSK9 is proceeded towards the secretory pathway.

Additionally to this mature PCSK9 form, another truncated (furin cleaved) form of PCSK9 has been observed in many cell lines and blood plasma. Human and mouse plasma contains the two forms of PCSK9, mature (aa153-692) and its truncated version (aa218-692) and in mouse plasma the truncated form can represent up to ~50% of the total plasma PCSK9. This furin cleaved truncated PCSK9 is a product of the cleavage of mature PCSK9 (aa153-692) at the site aa218-219, therefore termed as furin/PC5/6A cleavage site. Upon such cleavage a subsequent PCSK9 truncated fragment (aa219-692) (so called furin cleaved PCSK9) is formed.

Recent data confirmed the ability of both forms: mature PCSK9 (aa153-692) and furin cleaved PCSK9 (aa219-aa692) to bind the low density lipoprotein receptor (LDLR) and thus regulate its level and therefore LDLc levels.

In the process of binding to LDLR, PCSK9 catalytic domain interacts with LDLR through different sites. As a result of this binding PCSK9 is positioning itself with the EGF (B) domain of the LDLR in a structural conformation which again strengthens and optimizes this interaction through a second site known as region where the furin/PC5/6A cleavage site (aa218-219) is positioned.

Thus, therapeutics targeting the furin/PC5/6A cleavage PCSK9 site (aa218-219) among their ability to abrogate the proper positioning of PCSK9 towards LDLR would be able to block the action of furin on PCSK9. Such therapeutics will in parallel abrogate the indirect PCSK9/LDLR interaction (positioning), and will inhibit the production of a truncated LDLR binding active form of PCSK9 (aa219-692). This would lead to beneficial increase of LDLR and therefore beneficial lowering of plasma LDLc.

Clinical trials throughout the last 25 years confirmed the clear benefit in treating cardiovascular diseases and lowering circulating LDLc levels by using 3-hydroxy-3 methyl-glutaryl coenzyme A reductase inhibitors (Statins). Statins are acting by inhibiting the hepatic cholesterol biosynthesis leading to subsequent increase in the Sterol-Regulatory Element Binding Protein (hereafter called SREBP). SREBP is a regulator of genes involved in the lipid homeostasis, such as LDLR. And the raised SREBP leads to increase LDLR protein levels and subsequent increase uptake of LDLc from the circulation.

Statins are the most common used therapy against dyslipidemia. But despite their efficacy, the treatment with statins is quite often linked to adverse effects such as raised liver enzymes, muscle pain and myositis. In addition, significant number of statin treated patients fails to reach their goals in term of beneficial LDLc management and some of them are even statin intolerant. Interestingly, by acting on the SREBP statins not only increase the LDLR but also elevate the PCSK9 expression, leading to counteracting pharmacologic effect.

Thus, a combination of statins together with an anti-PCSK9 therapy was considered as promising approach for the LDLc management with potency of synergistic/additive effect in comparison to individual treatment.

And considerably the anti-PCSK9 therapies became even more attractive potential future LDLc modulator. That is suitable not only as a monotherapy, but also as a novel adjuvant therapy for most recommended and used current therapies such as statins or other substances such as fibrates or nicotinic acid. Meanwhile, several different strategies to suppress the synthesis or function of PCSK9 have been established. During the last decade approaches for inhibiting the synthesis by gene silencing with antisense-oligonucleotides (ASO), locked nucleic acid antisense-oligonucleotides (LNO-ASO) and siRNA have been quite actively developed. In addition, the ASO technology for inhibition of apolipoprotein-B has been successfully applied and recently approved by the Food and Drug Administration (FDA). In fact, application of siRNA against PCSK9 in monkeys (*Macaca fascicularis*) led to a significant reduction of total cholesterol. In general, the outcome from the different methods for PCSK9 gene silencing is controversial and apparently depends on the specificity of the approach. Two clinical phases I using siRNA and LNA-oligonucleotide faced some challenges, and were premature termination for uncertain reasons. However, on the other side a third clinical trial Phase I with inhibiting PCSK9 by siRNA was successfully terminated.

Other promising therapeutic approaches for inhibition of PCSK9-LDLR interaction by mimetic peptides and adnectins have been designed. But despite the different possibilities for inhibition, one of the most advanced approaches for reduction of LDLc by modulating PCSK9 are anti-PCSK9 monoclonal antibodies. To date, many clinical studies evaluating anti-PCSK9 monoclonal antibodies are currently ongoing. In Phase I clinical trials with healthy subjects, a single dose of anti-PCSK9 monoclonal antibody introduced intravenous or subcutaneously was able to reduce the LDLc levels up to 67%. Moreover, the same mAB applied subcutaneously bi-weekly or in 4 weeks interval in subjects on statin treatment succeeded a reduction of LDLc up to 81%. In addition, a phase II clinical trial with the same monoclonal antibody (bi-weekly treatment) in statin intolerant patients lowered the LDLc in the range of 41-66%. Those studies, confirmed that anti-PCSK9 therapy is efficient not only in healthy subjects, but also in statin treated and statin intolerant population. Furthermore, based on the positive outcome from the finalized clinical trials Phase III clinical trials to evaluate the effect of the mAB anti-PCSK9 therapy on patients with history of a prior myocardial infarction or stroke, coronary risk factors and coronary syndrome were performed and recently reported as meeting co-primary endpoints. However, one major issue of the PCSK9 monoclonal antibody therapies is the lack of a long-term persistent LDLc management.

WO 2009/055783 A2, WO 2009/100297 A1, WO 2010/057242 A2, WO 2011/02757 A2, WO 2011/117401 A1, WO 2012/59573 A1 WO 2013/037889 A2 and WO 2013/148284 A1 disclose vaccines with antigenic PCSK9 peptides. Luo et al. (J. Lipid Res. 50(2009): 1581-1588) discloses function and distribution of circulating human PCSK9 expressed extrahepatically in transgenic mice.

An object of the present invention is to provide means and methods for reducing LDLc in an individual; it is a specific object of the present invention to provide new antigenic PCSK9 peptides as vaccines with improved antigenic potential and being efficient for reduction of cholesterol in vaccinated individuals.

The present invention concerns specific immunopotentiating variants (amino acid exchanges and optional truncations) of PCSK9 fragment consisting of amino acid residues 209 to 222 SEQ ID NO: 1.

The peptides of the present invention are so-called VARIOTOPE®s i.e. amino acid variations of the original, native sequence of the peptide PEEDGTRFHRQASK (SEQ ID NO: 1). VARIOTOPE®s have an amino acid sequence which is different from the original protein/peptide sequence from which they are derived. The VARIOTOPE®s according to the present invention are considered as foreign by the immune system and therefore do not need to break self-tolerance.

The present invention relates to a vaccine, vaccine composition or composition comprising at least one peptide consisting of a VARIOTOPE® peptide or a peptide fragment thereof, derived from the PCSK9 fragment consisting of amino acid residues 209 to 222 (SEQ ID NO: 1).

The present invention therefore provides a vaccine comprising at least one peptide consisting of 9 to 25 amino acid residues, said peptide being a variant of the peptide PEEDGTRFHRQASK (SEQ ID NO: 1) with an increased immunogenicity in mammals, especially humans, compared to PEEDGTRFHRQASK (SEQ ID NO: 1) and wherein said variant is characterised by at least one and at most four amino acid exchanges compared to PEEDGTRFHRQASK (SEQ ID NO: 1).

Preferably, the vaccine according to the present invention comprises at least one peptide consisting of 9 to 25 amino acid residues, said peptide having or comprising the amino acid sequence $$X_1X_2EDGX_6RFX_9X_{10}X_{11}X_{12}X_{13}X_{14}, \quad (SEQ\ ID\ NO:\ 46)$$

wherein $X_1$ is an amino acid residue selected from the group consisting of lysine, threonine, alanine and proline, preferably alanine or proline, $X_2$ is glutamine or aspartic acid, preferably aspartic acid, $X_6$ is threonine or serine, $X_9$ is an amino acid residue selected from the group consisting of histidine, alanine and serine $X_{10}$ is an amino acid residue selected from the group consisting of arginine, alanine, glutamine, lysine, methionine, proline and serine, preferably arginine, serine or alanine, $X_{11}$ is an amino acid residue selected from the group consisting of glutamine, alanine, glutamic acid, lysine, threonine, and arginine, preferably glutamine, lysine, arginine, and threonine, $X_{12}$ is an amino acid residue selected from the group consisting of alanine, serine and threonine, preferably alanine or serine, $X_{13}$ is an amino acid residue selected from the group consisting of serine, alanine, and asparagine, preferably serine, $X_{14}$ is an amino acid residue selected from the group consisting of lysine, alanine, arginine, leucine, serine, threonine, and valine, preferably lysine or serine, or a fragment of SEQ ID NO: 46 having at least 9 consecutive amino acid residues, and wherein SEQ ID NO: 46 is not PEEDGTRFHRQASK (SEQ ID NO: 1) or an N- or C-terminally truncated fragment thereof.

According to a preferred embodiment of the present invention, the vaccine comprise a peptide that consists or comprises an amino acid sequence selected from the group consisting of AEEDGTRFHRQASK (SEQ ID NO: 2), PEEDGTRFARQASK (SEQ ID NO: 4), PEEDGTRFHAQASK (SEQ ID NO: 5), PEEDGTRFHRAASK (SEQ ID NO: 6), PEEDGTRFHRQAAK (SEQ ID NO: 7), PEEDGTRFHRQASA (SEQ ID NO: 8), TEEDGTRFHRQASK (SEQ ID NO: 9), PQEDGTRFHRQASK (SEQ ID NO: 10), PEEDGSRFHRQASK (SEQ ID NO: 12), PEEDGTRF- HQQASK (SEQ ID NO: 13), PEEDGTRFHKQASK (SEQ ID NO: 14), PEEDGTRFHMQASK (SEQ ID NO: 15), PEEDGTRFHREASK (SEQ ID NO: 16), PEEDGTRFHRRASK (SEQ ID NO: 17), PEEDGTRFHRKASK (SEQ ID NO: 18), PEEDGTRFHRQSSK (SEQ ID NO: 19), PEEDGTRFHRQANK (SEQ ID NO: 21), PEEDGTRFHRQASR (SEQ ID NO: 23), PEEDGTRFHRQASL (SEQ ID NO: 24), KEEDGTRFHRQASK (SEQ ID NO: 25), PEEDGTRFSRQASK (SEQ ID NO: 29), PEEDGTRFHPQASK (SEQ ID NO: 34), PEEDGTRFHSQASK (SEQ ID NO: 35), PEEDGTRFHRTASK (SEQ ID NO: 36), PEEDGTRFHRQTSK (SEQ ID NO: 37), PEEDGTRFHRQASS (SEQ ID NO: 38), PEEDGTRFHRQAST (SEQ ID NO: 39), PEEDGTRFHRQASV (SEQ ID NO: 40), PEEDGSRFHKQASK (SEQ ID NO: 41), PEEDGSRFHMQASK (SEQ ID NO: 42), PEEDGSRFHRRASK (SEQ ID NO: 43), and PEEDGSRFHRQATK (SEQ ID NO: 44); preferably AEEDGTRFHRQASK (SEQ ID NO: 2), PEEDGTRFARQASK (SEQ ID NO: 4), PEEDGTRFHAQASK (SEQ ID NO: 5), PEEDGTRFHRAASK (SEQ ID NO: 6), PEEDGTRFHRQASA (SEQ ID NO: 8), TEEDGTRFHRQASK (SEQ ID NO: 9), PQEDGTRFHRQASK (SEQ ID NO: 10), PEEDGTRFHRRASK (SEQ ID NO: 17), PEEDGTRFHRKASK (SEQ ID NO: 18), PEEDGTRFHRQSSK (SEQ ID NO: 19), PEEDGTRFSRQASK (SEQ ID NO: 29), PEEDGTRFHPQASK (SEQ ID NO: 34), PEEDGTRFHSQASK (SEQ ID NO: 35), PEEDGTRFHRTASK (SEQ ID NO: 36), PEEDGTRFHRQTSK (SEQ ID NO: 37), PEEDGTRFHRQASS (SEQ ID NO: 38), PEEDGTRFHRQASV (SEQ ID NO: 40), PEEDGSRFHKQASK (SEQ ID NO: 41), PEEDGSRFHRRASK (SEQ ID NO: 43), and PEEDGSRFHRQATK (SEQ ID NO: 44); especially AEEDGTRFHRQASK (SEQ ID NO: 2), PEEDGTRFHAQASK (SEQ ID NO: 5), PQEDGTRFHRQASK (SEQ ID NO: 10), PEEDGTRFHRRASK (SEQ ID NO: 17), PEEDGTRFHRKASK (SEQ ID NO: 18), PEEDGTRFHRQSSK (SEQ ID NO: 19), PEEDGTRFSRQASK (SEQ ID NO: 29), PEEDGTRFHSQASK (SEQ ID NO: 35), PEEDGTRFHRTASK (SEQ ID NO: 36), PEEDGTRFHRQTSK (SEQ ID NO: 37), PEEDGTRFHRQASS (SEQ ID NO: 38), PEEDGSRFHKQASK (SEQ ID NO: 41) and PEEDGTRFHRQASK (SEQ ID NO: 43).

The peptides provided with the present invention are immunopotentiating variants of the native PCSK9 amino acid sequence PEEDGTRFHRQASK (SEQ ID NO: 1). The peptides according to the present invention have been diligently designed and selected to provide an improved immune response against PCSK9 under careful consideration of self-tolerance issues usually connected to vaccines relying on native PCSK9 sequences.

The peptides according to the present invention have amino acid variations compared to the native sequence PEEDGTRFHRQASK (SEQ ID NO: 1). According to a preferred embodiment, the number of variations (exchanged amino acid residues) does not exceed 3 amino acid residues. Preferably, the peptide according to the present invention has only one or two amino acid exchanges. It is surprising that with such few amino acid exchanges, immunopotentiating peptide variations could be provided, especially with regard to their other beneficial property, namely that these novel peptides do not have to break self-tolerance.

Preferred peptides according to the present invention have an increased immunogenicity, compared to the peptide PEEDGTRFHRQASK (SEQ ID NO: 1), of at least 50%, preferably at least 100%, especially at least 200%, as evidenced in a serum ELISA, for example as evidenced by the example below.

According to a preferred embodiment, the peptides in the vaccine of the present invention have an increased ability to reduce total cholesterol levels, compared to the peptide PEEDGTRFHRQASK (SEQ ID NO: 1), of at least 3%, preferably at least 5%, especially at least 10%, as evidenced in a serum cholesterol test (in absolute figures, the untreated comparison being 100%), for example as evidenced by the example below. For at least some of the peptides according to the present invention, such enhanced total cholesterol lowering levels compared to the native sequence has been experimentally confirmed in a scientifically accepted cholesterol model. Accordingly, the variant according to the present invention is preferably selected from the group consisting of AEEDGTRFHRQASK (SEQ ID NO: 2), TEEDGTRFHRQASK (SEQ ID NO: 9), PQEDGTRFHRQASK (SEQ ID NO: 10), PEEDGTRFHRRASK (SEQ ID NO: 17), PEEDGTRFHRKASK (SEQ ID NO: 18), PEEDGTRFHRQASR (SEQ ID NO: 23), and PEEDGTRFHRTASK (SEQ ID NO: 36). Although it is already surprising that a variant peptide of the native sequence has an increased immunogenicity, compared to the native sequence peptide PEEDGTRFHRQASK (SEQ ID NO: 1), it was even more surprising that such peptides can also—in a scientifically accepted cholesterol model—reduce total cholesterol more efficient than the corresponding native sequence.

The peptides contained in the vaccines according to the present invention are preferably coupled or fused to a pharmaceutically acceptable carrier, preferably a carrier protein, especially a protein comprising at least one T cell epitope.

The administration of a vaccine according to the present invention allows treating or preventing pathological conditions linked to PCSK9 and its role in diseases such as dyslipidemia, hyperlipidemia, hypercholesterolemia and/or atherosclerosis.

The peptides of the present invention are variants (amino acid exchanges and optional truncations) of the PCSK9 fragment having amino acid sequence PEEDGTRFHRQASK (SEQ ID NO: 1) and consist of 9 to 25 amino acid residues, preferably 9 to 20 amino acid residues, especially 9 to 15 amino acid residues. Specifically preferred peptides according to the present invention consist of 10, 11, 12, 13, 14 or 15 amino acid residues, preferably 13 or 14 amino acid residues, especially 14 amino acid residues. Although PCSK9 VARIOTOPE® peptides according to the present invention are preferably used in a form where the peptides consist of the sequences given (e.g. SEQ ID NOS 2-46; optionally with a linker attached to its N- or C-terminus, especially at its C-terminus; said linker being or containing preferably a cysteine residue, especially a cysteine residue at the C-terminus); however, it is also possible to use shortened or longer sequences (see e.g.: WO 2013/037889 A1). For example, it is possible to delete a single amino acid from the N- or C-terminus and arrive at a virtually comparable peptide vaccine with respect to immunogenicity or TC reduction. Preferably such deletion can be made at the C-terminus. In some instances, also longer deletions (i.e. two or more amino acids) may be possible (see specifically: WO 2013/037889 A1, additional experiments provided for IPRP (FIGS. 5/6)). On the other hand, it is also possible to add amino acid residues N- or C-terminally (preferably C-terminally) without significant change in the properties of these peptides with respect to the present invention (see e.g. Amar et al., AHA presentation 18960 (2014)). Addition of amino acid residues at the N- or C-terminus are preferably additions of further amino acid residues naturally occurring at this (added) site, i.e. providing the native sequence extension in such VARIOTOPE®s.

The vaccine of the present invention comprise at least one, at least 2, or at least 3, of the peptides defined herein and allows the active immunization of a mammal, in particular a human individual, where neutralizing antibodies to the PCSK9 are induced by vaccination with derived fragments, especially when coupled or fused to a peptide or polypeptide or a carrier protein (as a T cell epitope comprising molecule).

The peptide/carrier combination is mostly important since peptides of the present invention usually do not have the capacity to induce relevant amounts of antibodies when injected without coupling.

Thus the vaccine may comprise a combination of two or more peptides as disclosed herein. However, it is also possible that the vaccine of the present invention comprises next to one or more peptides linked to SEQ ID NO: 1 and as defined herein also other peptides such as mimotopes (i.e. mutants of PCSK9 fragments; EP12182241) or fragments of PCSK9 (see e.g. WO 2013/037889).

The peptides of the present invention can be chemically synthesized by methods which are well known in the art. Of course, it is also possible to produce the peptides of the present invention using recombinant methods. The peptides can also be produced in microorganisms such as bacteria, yeast or fungi, in eukaryotic cells such as mammalian or insect cells, or in a recombinant virus vector such as adenovirus, poxvirus, herpes virus, Simliki forest virus, baculovirus, bacteriophage, sindbis virus or Sendai virus. Suitable bacteria for producing the peptides include *E. coli*, *B. subtilis* or any other bacterium that is capable of expressing such peptides. Suitable yeast cells for expressing the peptides of the present invention include *Saccharomyces cerevisiae, Schizosaccharomyces pombe, Candida, Pichia pastoris* or any other yeast capable of expressing peptides. Corresponding means and methods are well known in the art. Also methods for isolating and purifying recombinantly produced peptides are well known in the art and include e.g. gel filtration, affinity chromatography, ion exchange chromatography etc.

The peptides according to the present invention are able to induce antibodies that specifically bind to human PCSK9 and inhibit the PCSK9-mediated degradation of LDLR.

To facilitate isolation of the peptides of the present invention, fusion polypeptides may be made wherein the peptides are translationally fused (covalently linked) to a heterologous polypeptide which enables isolation by affinity chromatography. Typical heterologous polypeptides are His-Tag (e.g. His6; 6 histidine residues (SEQ ID NO: 47)), GST-Tag (Glutathione-S-transferase) etc. The fusion polypeptide facilitates not only the purification of the peptides but can also prevent the degradation of the peptides during the purification steps. If it is desired to remove the heterologous polypeptide after purification the fusion polypeptide may comprise a cleavage site at the junction between the peptide and the heterologous polypeptide. The cleavage site may consist of an amino acid sequence that is cleaved with an enzyme specific for the amino acid sequence at the site (e.g. proteases).

The vaccine and peptides of the present invention can be administered to any kind of mammal including humans. It is however preferred to administer the vaccine and peptides of the present invention to humans.

According to the preferred embodiment of the present invention at least one peptide comprised in the vaccine of the present invention is selected from the group consisting of

| SEQ ID NO: 2:  | AEEDGTRFHRQASK, |
|---|---|
| SEQ ID NO: 4:  | PEEDGTRFARQASK, |
| SEQ ID NO: 5:  | PEEDGTRFHAQASK, |
| SEQ ID NO: 6:  | PEEDGTRFHRAASK, |
| SEQ ID NO: 7:  | PEEDGTRFHRQAAK, |
| SEQ ID NO: 8:  | PEEDGTRFHRQASA, |
| SEQ ID NO: 9:  | TEEDGTRFHRQASK, |
| SEQ ID NO: 10: | PQEDGTRFHRQASK, |
| SEQ ID NO: 12: | PEEDGSRFHRQASK, |
| SEQ ID NO: 13: | PEEDGTRFHQQASK, |
| SEQ ID NO: 14: | PEEDGTRFHKQASK, |
| SEQ ID NO: 15: | PEEDGTRFHMQASK, |
| SEQ ID NO: 16: | PEEDGTRFHREASK, |
| SEQ ID NO: 17: | PEEDGTRFHRRASK, |
| SEQ ID NO: 18: | PEEDGTRFHRKASK, |
| SEQ ID NO: 19: | PEEDGTRFHRQSSK |
| SEQ ID NO: 21: | PEEDGTRFHRQANK, |
| SEQ ID NO: 23: | PEEDGTRFHRQASR, |
| SEQ ID NO: 24: | PEEDGTRFHRQASL, |
| SEQ ID NO: 25: | KEEDGTREHRQASK, |
| SEQ ID NO: 29: | PEEDGTRFSRQASK, |
| SEQ ID NO: 34: | PEEDGTRFHPRQASK, |
| SEQ ID NO: 35: | PEEDGTRFHSQASK, |
| SEQ ID NO: 36: | PEEDGTRFHRTASK, |
| SEQ ID NO: 37: | PEEDGTRFHRQASK, |
| SEQ ID NO: 38: | PEEDGTRFHRQASS |
| SEQ ID NO: 39: | PEEDGTRFHRQAST, |
| SEQ ID NO: 40: | PEEDGTRFHRQASV, |
| SEQ ID NO: 41: | PEEDGSRFHKQASK, |
| SEQ ID NO: 42: | PEEDGSRFHMQASK, |
| SEQ ID NO: 43: | PEEDGSRFHRRASK, |
| SEQ ID NO: 44: | PEEDGSRFHRQATK; | and fragments thereof having a length of at least 9 amino acids.

Following peptides that do not have the capacity to elicit a humoral immune response targeting PCSK9, highlight that amino acid exchanges have to be accurately selected to result in immunogenic peptides inducing antibodies efficiently blocking PCSK9 function:

| SEQ ID NO: 26: | PEWDGTRFHRQASK, |
|---|---|
| SEQ ID NO: 28: | PEEDGTGFHRQASK, |
| SEQ ID NO: 32: | PEEDGTRFGRQASK. |

According to a particularly preferred embodiment of the present invention the at least one peptide comprised in the vaccine of the present invention is selected from the group consisting of

| | |
|---|---|
| SEQ ID NO: 2: | AEEDGTRFHRQASK, |
| SEQ ID NO: 4: | PEEDGTRFARQASK, |
| SEQ ID NO: 5: | PEEDGTRFHAQASK, |
| SEQ ID NO: 6: | PEEDGTRFHRAASK, |
| SEQ ID NO: 7: | PEEDGTRFHRQAAK, |
| SEQ ID NO: 8: | PEEDGTRFHRQASA, |
| SEQ ID NO: 9: | TEEDGTREHRQASK, |
| SEQ ID NO: 10: | PQEDGTREHRQASK, |
| SEQ ID NO: 12: | PEEDGSRFHRQASK, |
| SEQ ID NO: 13: | PEEDGTRFHQQASK, |
| SEQ ID NO: 14: | PEEDGTRFHKQASK, |
| SEQ ID NO: 15: | PEEDGTRFHMQASK, |
| SEQ ID NO: 16: | PEEDGTRFHREASK, |
| SEQ ID NO: 17: | PEEDGTREHRRASK, |
| SEQ ID NO: 18: | PEEDGTRFHRKASK, |
| SEQ ID NO: 19: | PEEDGTREHRQSSK |
| SEQ ID NO: 21: | PEEDGTRFHRQANK, |
| SEQ ID NO: 23: | PEEDGTREHRQASR, |
| SEQ ID NO: 24: | PEEDGTREHRQASL, |
| SEQ ID NO: 25: | KEEDGTREHRQASK, |
| SEQ ID NO: 29: | PEEDGTRFSRQASK, |
| SEQ ID NO: 34: | PEEDGTRFHPQASK, |
| SEQ ID NO: 35: | PEEDGTRFHSQASK, |
| SEQ ID NO: 36: | PEEDGTRFHRTASK, |
| SEQ ID NO: 37: | PEEDGTRFHRQTSK, |
| SEQ ID NO: 38: | PEEDGTRFHRQASS, |
| SEQ ID NO: 39: | PEEDGTRFHRQAST, |
| SEQ ID NO: 40: | PEEDGTRFHRQASV, |
| SEQ ID NO: 41: | PEEDGSRFHKQASK, |
| SEQ ID NO: 42: | PEEDGSRFHMQASK, |
| SEQ ID NO: 43: | PEEDGSRFHRRASK, |
| SEQ ID NO: 44: | PEEDGSRFHRQATK; |

TABLE A

| Amino acid residues | | |
|---|---|---|
| Amino acid | Three letter code | One letter code |
| alanine | ala | A |
| arginine | arg | R |
| asparagine | asn | N |
| aspartic acid | asp | D |
| cysteine | cys | C |
| glutamic acid | glu | E |
| glutamine | gln | Q |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

According to a particularly preferred embodiment at least one peptide comprised in the vaccine of the present invention comprises at its N- and/or C-terminus at least one cysteine residue bound directly or via a spacer sequence thereto.

This cysteine residue may serve as a reactive group in order to bind the peptide to another molecule or a carrier. For instance, this group may be used to bind the peptide to a carrier protein. The cysteine residue can be bound directly to the peptides of the present invention or via a spacer sequence. The spacer sequence comprises preferably at least one, preferably at least two, more preferably at least three, even more preferably at least four, and optionally a maximum of ten, preferably a minimum of five small non-polar amino acid residues such as glycines.

It is, however, clear that such cysteine residue or other amino acid linkers (such as, e.g. CG-, CGG-, -GC, -GGC, etc.) are not to be regarded as (N- or C-terminal) exchanges or variations of the native PCSK9 peptide epitope PEEDGTRFHRQASK (SEQ ID NO: 1) or fragments thereof, but additions to the epitope sequence eliciting the specific antibody response in the vaccinated individual.

According to a preferred embodiment of the present invention the vaccine according to the present invention comprises a protein carrier, preferably a protein carrier selected from the group consisting of keyhole limpet haemocyanin (KLH), CRM (preferably CRM197), tetanus toxoid (TT), diphtheria toxin (DT), protein D or any other protein or peptide containing helper T-cell epitopes.

According to the present invention the peptide is preferably coupled or fused to a pharmaceutically acceptable carrier, preferably KLH (Keyhole Limpet Hemocyanin), CRM, tetanus toxoid, albumin-binding protein, bovine serum albumin, a dendrimer, peptide linkers (or flanking regions) as well as the adjuvant substances described in Singh et al. (Singh et al., Nat. Biotech. 17, (1999): 1075-1081 (in particular those in Table 1 of that document)), and O'Hagan et al. (O'Hagan and Valiante, Nature Reviews, Drug Discovery 2 (9); (2003): 727-735 (in particular the endogenous immuno-potentiating compounds and delivery systems described therein)), or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art.

Alternatively it is also possible to fuse the at least one peptide of the present invention to a protein carrier by methods known in the art. Such proteins comprise a peptide as described herein together with an unrelated immunogenic protein. Preferably the immunogenic protein is capable of eliciting a recall response. Examples of such proteins include tetanus, tuberculosis, hepatitis proteins and protein D, a surface protein of the gram-negative bacterium *Haemophilus* influenza B (WO 91/18926). Preferably a protein D derivative is used which comprises approximately the first third of the protein (e.g., the first N-terminal 100-110 amino acids) and which may be lipidated. Another carrier which may be used to provide fusion proteins may be the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43; (1986):265-292). LYTA is an autolysin that specifically degrades certain bonds in the peptidoglycan backbone. Within a preferred embodiment, a repeat portion of LYTA may be incorporated into a fusion protein. A repeat portion is found in the C-terminal region starting at residue 178. A particularly preferred repeat portion incorporates residues 188-305.

According to a preferred embodiment of the present invention the peptide is formulated with an adjuvant, preferably adsorbed to aluminium hydroxide (Alhydrogel, Al(OH)$_3$).

The vaccine according to the present invention may be formulated with an adjuvant, preferably a low soluble aluminum composition, in particular aluminum hydroxide. Of course, also adjuvants like MF59, aluminum phosphate, calcium phosphate, cytokines (e.g. IL-2, IL-12, GM-CSF), saponins (e.g. QS21), MDP derivatives, CpG oligonucleotides, LPS, MPL, polyphosphazenes, emulsions (e.g. Freund's, SAF), liposomes, virosomes, iscoms, cochleates, PLG microparticles, poloxamer particles, virus-like particles, heat-labile enterotoxin (LT), cholera toxin (CT), mutant toxins (e.g. LTK63 and LTR72), microparticles and/or polymerized liposomes may be used.

Suitable adjuvants are commercially available as, for example, AS01B, AS02A, AS15, AS-2 and derivatives thereof (GlaxoSmithKline, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7 or -12 may also be used as adjuvants.

Preferred adjuvants for use in eliciting a predominantly Th1-type response include, for example, a combination of monophosphoryl lipid A, preferably 3-O-deacylated monophosphoryl lipid A (3D-MPL), optionally with an aluminum salt (see, for example, Ribi et al., Immunology and Immunopharmacology of Bacterial Endotoxins, Plenum Publ. Corp., NY, (1986): 407-419; GB 2122204B; GB 2220211; and U.S. Pat. No. 4,912,094). A preferred form of 3D-MPL is an emulsion having a small particle size less than 0.2 mm in diameter, and its method of manufacture is disclosed in WO 94/21292. Aqueous formulations comprising monophosphoryl lipid A and a surfactant have been described in WO 98/43670. Exemplified preferred adjuvants include AS01B (MPL and QS21 in a liposome formulation), 3D-MPL and QS21 in a liposome formulation, AS02A (MPL and QS21 and an oil-in-water emulsion), 3D-MPL and QS21 and an oil-in-water emulsion, and AS 15. MPL adjuvants are disclosed e.g. in U.S. Pat. No. 4,436,727; U.S. Pat. No. 4,877,611; U.S. Pat. No. 4,866,034 and U.S. Pat. No. 4,912,094.

CpG-containing oligonucleotides (in which the CpG dinucleotide is unmethylated) also induce a predominantly Th1 response. CpG is an abbreviation for cytosine-guanosine dinucleotide motifs present in DNA. Such oligonucleotides are well known and are described, for example, in WO 96/02555, WO 99/33488, U.S. Pat. No. 6,008,200 and U.S. Pat. No. 5,856,462. Immunostimulatory DNA sequences are also described, for example, by Sato et al., Science 273; (1996):352. CpG when formulated into vaccines is generally administered in free solution together with free antigen (WO 96/02555; McCluskie and Davis, supra) or covalently conjugated to an antigen (WO 98/16247), or formulated with a carrier such as aluminium hydroxide ((Hepatitis surface antigen) Davis et al., supra; Brazolot-Millan et al., PNAS USA, 95(26), (1998):15553-8). CpG is known in the art as being an adjuvant that can be administered by both systemic and mucosal routes (WO 96/02555, EP 0 468 520, Davis et al., J. Immunol, 160(2), (1998):870-876; McCluskie and Davis, J. Immunol., 161(9), (1998): 4463-6).

Another preferred adjuvant is a saponin or saponin mimetics or derivatives, preferably QS21 (Aquila Biopharmaceuticals Inc.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210. Additional saponin adjuvants of use in the present invention include QS7 (described in WO 96/33739 and WO 96/11711) and QS17 (described in U.S. Pat. No. 5,057,540 and EP 0 362 279 B1).

Other preferred adjuvants include Montanide ISA 720 (Seppic, France), SAF (Chiron, California, United States), ISCOMS (CSL), MF-59 (Chiron), the SEAS series of adjuvants (e.g., SBAS-2, AS2', AS2, SBAS-4, or SBAS6, available from GlaxoSmithKline), Detox (Corixa), RC-529 (Corixa, Hamilton, Mont.) and other amino-alkyl glucosaminide 4-phosphates (AGPs). Further example adjuvants include synthetic MPL and adjuvants based on Shiga toxin B subunit (see WO 2005/112991). It is particularly preferred to use aluminium hydroxide as adjuvant.

The vaccine of the present invention may be administered by any suitable route known for vaccines, preferably subcutaneously, intramuscularly, intradermally, or intravenously. Depending on the route of administration, the medicament may comprise respective carriers, adjuvants, and/or excipients.

A vaccine which comprises a peptide of the present invention and the pharmaceutically acceptable carrier may be administered by any suitable mode of application, e.g. intradermally (i.d.), intraperitoneally (i.p.), intramuscularly (i.m.), intranasally, orally, subcutaneously (s.c.), etc. and in any suitable delivery device (O'Hagan et al., Nature Reviews, Drug Discovery 2 (9), (2003), 727-735). The peptides of the present invention are preferably formulated for intradermal, subcutaneous or intramuscular administration. Means and methods for obtaining respective formulations are known to the person skilled in the art.

According to a preferred embodiment of the present invention the vaccine is used for the treatment and/or prevention of disorders caused by hyperlipidemia, hypercholesterolemia and/or atherosclerosis, preferably cardiovascular diseases, stroke or peripheral vascular diseases and other diseases linked to PCSK9, e.g. neoplastic diseases, such as melanoma and liver cancer metastasis (Sun et al, Neoplasia, 14(12) 2012, 1122-1131) in particular in mammals, preferably in humans.

As outlined, the peptides of the present invention are able to induce the formation of antibodies which are able to bind specifically PCSK9. The interaction of the antibodies with PCSK9 leads to the increase of low density lipoprotein receptor in liver hepatocytes in vivo, increased plasma cholesterol uptake and subsequent reduction of the plasma LDL cholesterol levels and thus the overall cholesterol levels.

In particular, the present invention relates to antibodies able to bind the aa209-222 PCSK9 region and negatively influence the PCSK9/LDLR interaction and therefore beneficially reduce plasma cholesterol. Those antibodies also block the cleavage of the mature PCSK9 (aa153-692) protein by furin and therefore inhibit the production of LDLR binding truncated form of PCSK9 (aa219-692). Additionally, the peptides of the present invention are able to induce the formation of antibodies which are able to bind PCSK9 in the region 209-222 and inhibit the process of furin cleavage of the mature PCSK9.

The disease associated with atherosclerosis is preferably selected from the group consisting of peripheral arterial occlusive disease, coronary heart disease, apoplectic cerebral insultus and stroke.

The terms "diseases associated with hyperlipidemia, hypercholesterolemia and/or atherosclerosis" and "disorders caused by hyperlipidemia, hypercholesterolemia and/or atherosclerosis" refer to diseases which are a consequence of hyperlipidemia, hypercholesterolemia and atherosclerosis. These diseases include among others peripheral arterial occlusive disease, coronary heart disease and apoplectic cerebral insultus (see e.g. Steinberg, D. J Lipid Res 46(2005):179-190 and Steinberg, D. J Lipid Res 47(2006): 1339-1351). According to a preferred embodiment of the present invention the peptides of the present invention are administered to a mammal or an individual in an amount of 0.1 ng to 10 mg, preferably of 0.5 to 500 µg, more preferably 1 to 100 µg, per immunization. In a preferred embodiment these amounts refer to all peptides (if more than one peptide is used in the vaccine) present in the vaccine. In another preferred embodiment these amounts refer to each single fragment present in the vaccine. It is of course possible to provide a vaccine in which the peptides are present in different or equal amounts. However, the peptides of the present invention may alternatively be administered to a mammal or an individual in an amount of 0.1 ng to 10 mg, preferably 10 ng to 1 mg, in particular 100 ng to 300 µg/kg body weight.

The amount of peptides that may be combined with the carrier materials to produce a single dosage form will vary depending upon the host treated and the particular mode of administration. The dose of the vaccine may vary according to factors such as the disease state, age, sex and weight of the mammal or individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances. For instance, the peptides and vaccine of the present invention may be administered to an individual at intervals of several days, one or two weeks or even months or years depending always on the level of antibodies directed to PCSK9.

In a preferred embodiment of the present invention the peptide/vaccine is applied between 2 and 10, preferably between and 7, and most preferably up to 5. This number of immunizations may lead to a basic immunisation. In a particularly preferred embodiment the time interval between the subsequent vaccinations is chosen to be between 2 weeks and 5 years, preferably between 1 month and up to 3 years, more preferably between 2 months and 1.5 years. An exemplified vaccination schedule may comprise 3 to 4 initial vaccinations over a period of 6 to 8 weeks and up to 6 months, preferably followed with further administrations after such initial vaccinations. Thereafter the vaccination may e.g. be repeated every two to ten years. The repeated administration of the peptide/vaccine of the present invention may maximize the final effect of a therapeutic vaccination.

The vaccine of the present invention may also comprise antigens derived from other proteins. For examples proteins involved in the regulation of the LDL and/or HDL levels within a human body. For instance, the PCSK9 fragments of the present invention may be combined with epitopes derived from human CETP protein. The vaccine of the present invention may also comprise antigens derived from a different epitope of the PCSK9 protein.

The vaccine of the present invention may also comprise antigens derived from other proteins suitable for the treatment of hyperlipidemia, hypercholesterolemia and/or atherosclerosis, preferably cardiovascular diseases, stroke or peripheral vascular diseases.

Typically, the vaccine contains the peptides of the present invention in an amount of 0.5 to 500 µg, preferably 1 to 100 µg and alternatively from 0.1 ng to 10 mg, preferably 10 ng to 1 mg, in particular 100 ng to 100 µg, or, alternatively, e.g. 100 fmol to 10 µmol, preferably 10 pmol to 1 µmol, in particular 100 pmol to 100 nmol. Typically, the vaccine may also contain auxiliary substances, e.g. buffers, stabilizers etc.

Yet another aspect of the present invention relates to a method for treating an individual suffering or at risk to suffer from atherosclerosis or a disease associated with atherosclerosis in the course of which a peptide or vaccine according to the present invention is administered to said individual.

Next to the vaccine of the present invention, the individual to be treated may receive also other active ingredients known to influence the LDL and/or HDL levels in humans and mammals such as statins, fibrates, nicotinic acid, cholesterol uptake inhibitor (e.g. ezetimibe), ApoA1 Milano, delipidated HDL, plant sterols. It is particularly preferred to administer to an individual the vaccine of the present invention together (i.e. at the same time, consecutively etc.) with statins. The vaccine of the present invention can also be combined with methods like LDL apheresis. LDL apheresis is a form of apheresis to eliminate the cholesterol-containing particle low-density lipoprotein (LDL) from the bloodstream. Typically LDL apheresis works by leading venous blood through a column coated with antibodies to apolipoprotein B (the main protein of LDL particles), dextran sulfate or polyacrylate, or by precipitating LDL with heparin at low pH. Respective methods are known to a person skilled in the art.

The term "preventing", as used herein, covers measures not only to prevent the occurrence of disease, such as risk factor reduction, but also to arrest its progress and reduce its consequences once established.

As used herein, the term "treatment" or grammatical equivalents encompasses the improvement and/or reversal of the symptoms of disease. A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder as well as those in which a disease and/or disorder is to be prevented (e.g., using a prophylactic treatment of the present invention).

The present invention is further illustrated by the following example and the figures, however, without being restricted thereto.

FIG. 1 Protein ELISA

FIGS. 1A and 1B show comparison of the mean titers (n=5 mice/group) against human PCSK9 protein induced by the indicated sequences.

The data reveal the ability of the selected VARIOTOPEs® to induce higher antibodies titers against human PCSK9 protein in comparison to the native sequence (SEQ ID NO: 1: PEEDGTRFHRQASK). FIG. 1A discloses SEQ ID NOS 1-40, respectively, in order of appearance. FIG. 1B discloses SEQ ID NOS 1 and 41-45, respectively, in order of appearance.

FIG. 2 % Total Cholesterol in comparison to the negative control group set as 100%.

FIG. 2A shows comparison of the % mean (n=3 mice/group) total cholesterol levels of mice immunized with selected immunogenic VARIOTOPE®s (SEQ ID NO: 10: PQEDGTRFHRQASK, SEQ ID NO: 17: PEEDGTRFHRRASK, SEQ ID NO: 18: PEEDGTRFHRKASK, SEQ ID NO: 23: PEEDGTRFHRQASR) in comparison to a negative control group immunized with irrelevant peptide and to the native original PCSK9 sequence (SEQ ID NO: 1: PEEDGTRFHRQASK). Note the ability of the VARIOTOPE®s to reduce the total cholesterol levels to similar or even lower levels in comparison to the native sequence.

FIG. 2B shows comparison of the mean (n=5 mice/group) total cholesterol levels of mice immunized with selected immunogenic VARIOTOPE® (SEQ ID NO: 36: PEEDGTRFHRTASK) in comparison to a negative control group immunized with irrelevant peptide and to the native original PCSK9 sequence (SEQ ID NO: 1: PEEDGTRFHRQASK). Note the ability of the VARIOTOPE® to reduce the total cholesterol levels stronger in comparison to the native sequence.

FIG. 2C shows comparison of the % (n=5 mice/group) total cholesterol levels of mice immunized with selected VARIOTOPE® with multiple aa exchanges (SEQ ID NO: 41: PEEDGSRFHKQASK and SEQ ID NO: 44: PEEDGSRFHRQATK) in comparison to a negative control group immunized with irrelevant peptide and to the native original PCSK9 sequence (SEQ ID NO: 1: PQEDGTRFHRQASK). Note the ability of the VARIOTOPE®s to reduce the total cholesterol levels stronger in comparison to the native sequence.

FIG. 3. Inhibition of furin cleavage and production of truncated furin cleaved PCSK9.

FIG. 3 reveals the ability of selected high immunogenic VARIOTOPE®s (SEQ ID NO: 10: PQEDGTRFHRQASK, SEQ ID NO: 17: PEEDGTRFHRRASK, SEQ ID NO: 18: PEEDGTRFHRKASK, SEQ ID NO: 23: PEEDGTRFHRQASR) to induce antibodies that are able to inhibit the furin cleavage of the mature PCSK9 (aa153-692) and thus abrogate the production of truncated PCSK9 (~50 kDa product) (aa219-692). The cleavage process is compared to negative control (PCSK9 incubated with plasma from mice injected with irrelevant peptide) and positive controls (huPCSK9 incubated with or without furin).

EXAMPLES

Materials and Methods

Figure 1A:
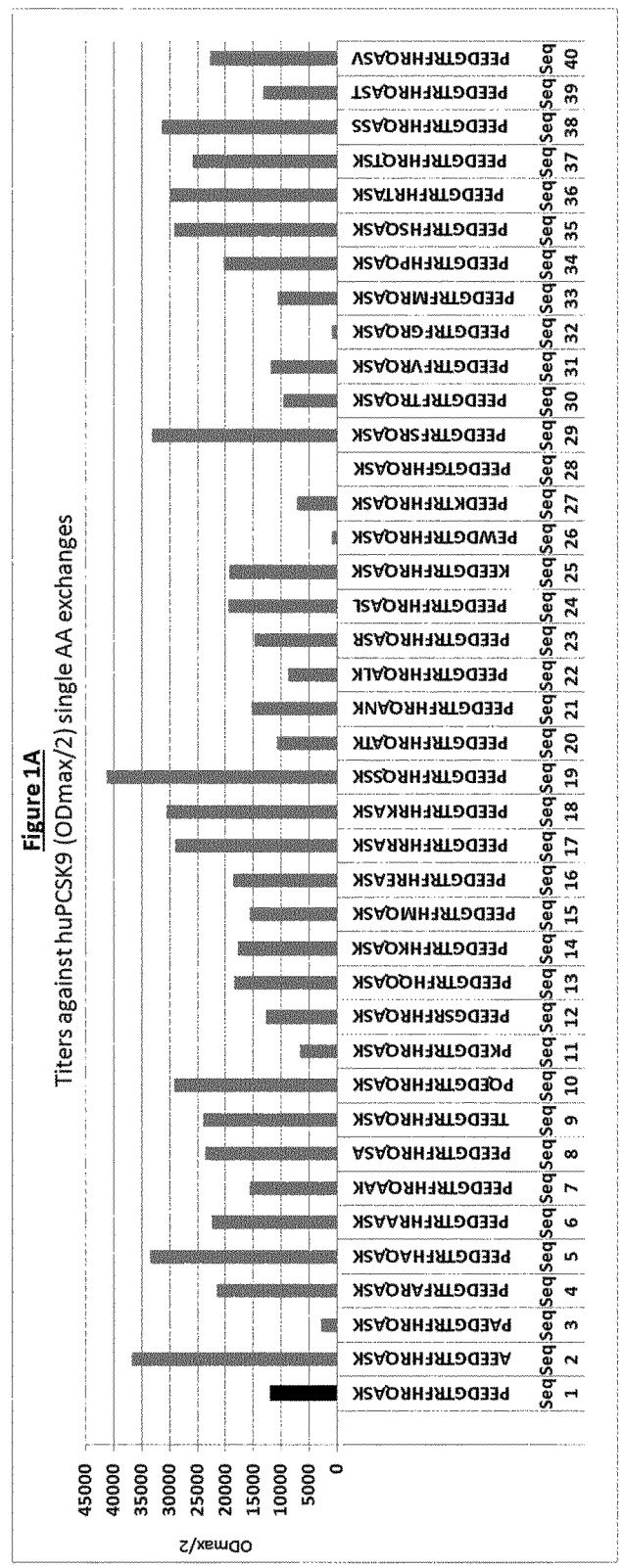

Vaccine:

The peptides were conjugated via the heterobifunctional linker GMBS (4-Maleimidobutyric acid N-hydroxysuccinimide ester) to KLH (Keyhole Limpet Hemocyanin).

Animal Experiments:

5 BALB/c mice were subcutaneously immunized. Mice had access to food and water ad libitum and were kept under a 12 h light/dark cycle. The age of mice at the beginning of experiments was 8 to 10 weeks.

Mice were injected four times in 2 week intervals with 15 µg of net peptide coupled to KLH and adsorbed to Alhydrogel as adjuvant in a volume of 1 ml in total.

Blood was taken approximately 2 weeks after the final injection.

Protein ELISA:

To determine the immunogenicity of the vaccines, and thus to identify the amount of PCSK9 specific antibodies in the plasma of immunized animals, ELISA immunoassay was performed. The ELISA immunoassay generates a signal which can be easily quantified and represents a quantitative measure of the amount of vaccine induced PCSK9-specific antibodies. Thus the titers as measured by ELISA correlate directly with the amount (µg/ml) of target specific antibodies in the plasma sample of treated animals. All plasma samples were collected two weeks after the final immunization and equality treated. In order to have a direct comparison, the quantitative evaluation by the PCSK9 Protein ELISA immunoassay of the vaccine induced PCSK9-specific antibodies and the comparison to their relative controls (originals sequence and negative control) was performed for all samples simultaneously. For this purpose, ELISA plates were coated with recombinantly expressed human PCSK9 protein. Unspecific binding was blocked by incubation with blocking buffer (1% BSA in PBS). Appropriate serum dilutions (with a starting dilution of 1:100) were added to the wells, serially diluted 1:2 fold (12 dilution steps) and incubated for approximately 1 hour. Bound antibodies were detected by incubation with anti-mouse IgG antibody, ABTS was added as substrate and the OD at 405 nm was measured. As negative control sera from the control group injected with an irrelevant peptide were analyzed. The titers were defined as the dilution of the serum where 50% of the ODmax in the assay is reached.

Total Cholesterol Assay:

All plasma samples were collected two weeks after the final immunization and equality treated. Total cholesterol (TC) measurements were performed simultaneously for all samples and side by side compared to their related controls (originals sequence and negative control). The simultaneous quantitative measurement of the plasma TC levels in mg/dL was measured by LabAssay™ Cholesterol Kit (Wako). In details, upon incubation with the chromogen reagent containing cholesterol esterase, the cholesterol esters in the samples were decomposed into free cholesterol and fatty acids. Subsequently the free cholesterol was oxidized by the cholesterol oxidase, leading to the simultaneously release of hydrogen peroxide. The produced hydrogen peroxide let DAOS and 4-Aminoantipyrin oxidize and condensate quantitatively by peroxidase (HRP), which produced blue pigment. Optical density was measured at 600 nm and quantification of the TC was calculated according to a standard curve.

Inhibition of Furin Cleavage

The furin cleavage reaction was performed with 2 Units Furin (~110 ng) (New England Biolabs) in PCSK9 buffer containing 100 mM Hepes Buffer pH 7.5, 5% Triton-X and 1 mM CaCl. In details, 4 µl mouse plasma from VARIOTOPE®s vaccinated mice was incubated with 250 ng biotinylated huPCSK9 (BPS Bioscience) in PCSK9 buffer for 1 h at room temperature. Subsequently, 2U Furin (~110 ng) (New England Biolabs) was added to the reaction solution and incubated over night at RT. The reaction product was analyzed by SDS-PAGE under reducing conditions.

Results:
1. Sequence information and titers against huPCSK9 (ODmax/2):

| SEQ ID NO: | Sequence | ODmax/2 |
|---|---|---|
| 1 | PEEDGTRFHRQASK | 12074 |
| 2 | AEEDGTRFHRQASK | 36869 |
| 3 | PAEDGTRFHRQASK | 2774 |
| 4 | PEEDGTRFARQASK | 21494 |
| 5 | PEEDGTRFHAQASK | 33442 |
| 6 | PEEDGTRFHRAASK | 22475 |
| 7 | PEEDGTRFHRQAAK | 15676 |
| 8 | PEEDGTRFHRQASA | 23638 |
| 9 | TEEDGTRFHRQASK | 23944 |
| 10 | PQEDGTRFHRQASK | 29228 |
| 11 | PKEDGTRFHRQASK | 6610 |
| 12 | PEEDGSRFHRQASK | 12636 |
| 13 | PEEDGTRFHQQASK | 18490 |
| 14 | PEEDGTRFHKQASK | 17795 |
| 15 | PEEDGTRFHMQASK | 15556 |
| 16 | PEEDGTRFHREASK | 18670 |
| 17 | PEEDGTRFHRRASK | 28996 |
| 18 | PEEDGTRFHRKASK | 30537 |
| 19 | PEEDGTRFHRQSSK | 41310 |
| 20 | PEEDGTRFHRQATK | 10813 |
| 21 | PEEDGTRFHRQANK | 15303 |
| 22 | PEEDGTRFHRQALK | 8694 |
| 23 | PEEDGTRFHRQASR | 14722 |
| 24 | PEEDGTRFHRQASL | 19471 |
| 25 | KEEDGTRFHRQASK | 19315 |
| 26 | PEWDGTRFHRQASK | 840 |
| 27 | PEEDKTRFHRQASK | 7154 |
| 28 | PEEDGTGFHRQASK | 0 |
| 29 | PEEDGTRFSRQASK | 33111 |
| 30 | PEEDGTRFTRQASK | 9519 |
| 31 | PEEDGTRFVRQASK | 11850 |
| 32 | PEEDGTRFGRQASK | 822 |
| 33 | PEEDGTRFMRQASK | 10651 |
| 34 | PEEDGTRFHPQASK | 20318 |
| 35 | PEEDGTRFHSQASK | 29223 |
| 36 | PEEDGTRFHRTASK | 29984 |
| 37 | PEEDGTRFHRQTSK | 25826 |
| 38 | PEEDGTRFHRQASS | 31481 |
| 39 | PEEDGTRFHRQAST | 13172 |
| 40 | PEEDGTRFHRQASV | 22678 |
| 41 | PEEDGSRFHKQASK | 37296 |
| 42 | PEEDGSRFHMQASK | 18599 |
| 43 | PEEDGSRFHRRASK | 29435 |
| 44 | PEEDGSRFHRQATK | 20684 |
| 45 | PEEDGSRFHRRATK | 11097 |
| 46 | $X_1X_2EDGX_6RFX_9X_{10}X_{11}X_{12}X_{13}X_{14}$ | |

These results are also depicted in FIG. 1. According to the present invention, those VARIOPTOPEs® that have the potential to elicit a higher titer against huPCSK9 (e.g. measured as ODmax/2) according to the present example) are regarded as immunopotentiating variants of the native sequence PEEDGTRFHRQASK (SEQ ID NO: 1). A preferred VARIOPTOPE® according to the present invention has a pronounced immunopotentiating property (measured e.g. as an ODmax/2 in the present example of above 20000 or as a raising this effect to 150%, preferably of doubling of this effect, compared to the native sequence). An even more preferred VARIOPTOPE® according to the present invention has an even more pronounced immunopotentiating property (measured e.g. as an ODmax/2 in the present example of above 25000, preferably of above 30000; or as a tripling of this effect, compared to the native sequence).

2. Total Cholesterol in % compared to the control group set as 100% in mice immunized with VARIOTOPE®s with single AA exchange (SEQ ID NOS 10, 17, 18 and 23; FIGS. 2A and SEQ ID NO: 36 2B) and multiple exchanges (SEQ ID NOS 41, 44; FIG. 2C).

| FIG. 2A TC in % | | |
|---|---|---|
| SEQ ID NO: | Negative Control | 100 |
| 1 | PEEDGTRFHRQASK (original sequence) | 81 |
| 10 | PQEDGTRFHRQASK | 78 |
| 17 | PEEDGTRFHRRASK | 81 |
| 18 | PEEDGTRFHRKASK | 81 |
| 23 | PEEDGTRFHRQASR | 70 |

| FIG. 2B TC in % | | |
|---|---|---|
| SEQ ID NO: | Negative Control | 100 |
| 1 | PEEDGTRFHRQASK (original sequence) | 89 |
| 36 | PEEDGTRFHRTASK | 72 |

| FIG. 2C TC in % multiple AA exchanges | | |
|---|---|---|
| SEQ ID NO: | Negative Control | 100 |
| 1 | PEEDGTRFHRQASK (original sequence) | 81 |
| 41 | PEEDGSRFHKQASK | 66 |
| 44 | PEEDGSRFHRQATK | 74 |

These results are also depicted in FIG. 2. According to the present invention, those VARIOPTOPEs® that have the potential to elicit a comparable reduction of TC compared to the native sequence PEEDGTRFHRQASK (SEQ ID NO: 1) are preferred. Of course, an even more preferred VARIOPTOPE® according to the present invention has the ability to reduce TC to an even higher amount than the native sequence (measured e.g. as a reduction in % TC as measured in the present example of more than 5%, especially more than 10% (absolute, i.e. compared to the negative control), compared to the native sequence).

3. Western blot analysis reveals the ability of the induced antibodies upon immunization with SEQ ID NOS 10, 17, 18 and to inhibit the formation of truncated furin cleaved PCSK9 (a219-692; ~50 kDa) (see FIG. 3).

Reduction of Total Cholesterol (TC) in Treated Animals

Additional experiments were performed in order to deliver further experimental evidence showing that the capacity of selected VARIOTOPE® vaccine candidates have the ability to reduce total cholesterol (TC) in treated animals to a higher extent than a vaccine containing the corresponding native (original) sequence.

Peptides used for immunizations in the following experiments:

SEQ ID NO: 1:   PEEDGTRFHRQASK
                (original native Sequence)
SEQ ID NO: 2:   AEEDGTRFHRQASK
SEQ ID NO: 9:   TEEDGTRFHRQASK
SEQ ID NO: 10:  PQEDGTRFHRQASK
SEQ ID NO: 17:  PEEDGTRFHRRASK
SEQ ID NO: 18:  PEEDGTRFHRKASK
SEQ ID NO: 23:  PEEDGTRFHRQASR
SEQ ID NO: 36:  PEEDGTRFHRTASK
SEQ ID NO: 24:  PEEDGTRKHRQASL In order to evaluate the ability of selected VARIOTOPE® vaccine candidates to reduce TC and to compare the magnitude of TC reduction in VARIOTOPE® treated animals with the TC reduction in animals treated with a vaccine containing the original sequence, 5 to 10 mice per group were injected five times in 2 week intervals with vaccines containing 1 µg of net peptide. As usual, antigenic peptides were coupled to KLH and adsorbed to 0.2% Alhydrogel as adjuvant in a volume of 1 ml in total. For the described experiments GMP-like material was used. Blood samples were taken approximately 2 weeks after the final injection.

In a first experiment, vaccines containing the original sequence and containing the following VARIOTOPE®s were tested:

SEQ ID NO: 1:   PEEDGTRFHRQASK
SEQ ID NO: 9:   TEEDGTRFHRQASK
SEQ ID NO: 17:  PEEDGTRFHRRASK
SEQ ID NO: 18:  PEEDGTRFHRKASK
SEQ ID NO: 23:  PEEDGTRFHRQASR

In order to include a vaccine known to be able to reduce TC levels in treated animals but to be inferior in reducing TC levels compared to the vaccine containing the original sequence the following peptide vaccine was included in this experiment:

SEQ ID NO: 24:   PEEDGTRFHRQASL

Figure 4:
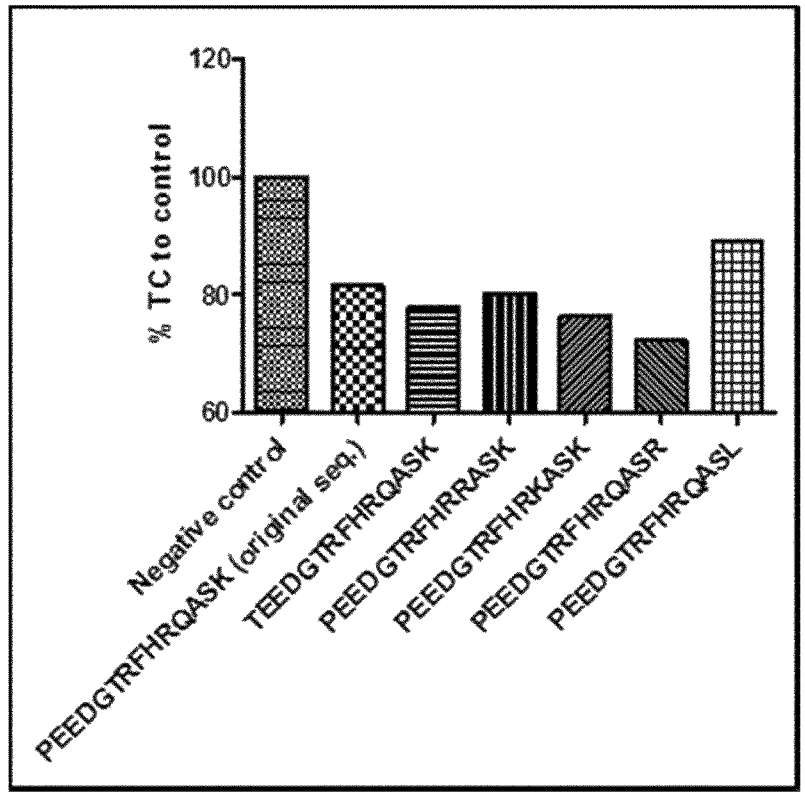
FIG. 4 shows % total cholesterol (TC) in comparison to the negative control group set as 100%. Figure discloses SEQ ID NOS 1, 9, 17, 18, 23, and 24, respectively, in order of appearance.

As already outlined above (FIG. 1A), all vaccine candidates are highly immunogenic and have the capacity to induce an antibody response that effectively bind to huPCSK9 as well as mouse PCSK9. In order to prove efficacy of the induced antibodies, TC measurements of blood samples derived from individual mice were performed. FIG. 4 depicts relative group mean TC values (in %) compared to the control group set as 100%. In this experiment 5 animals per group were immunized. As can be seen, in all vaccine treated groups TC values were significantly reduced in comparison to the control group.

Figure 5:
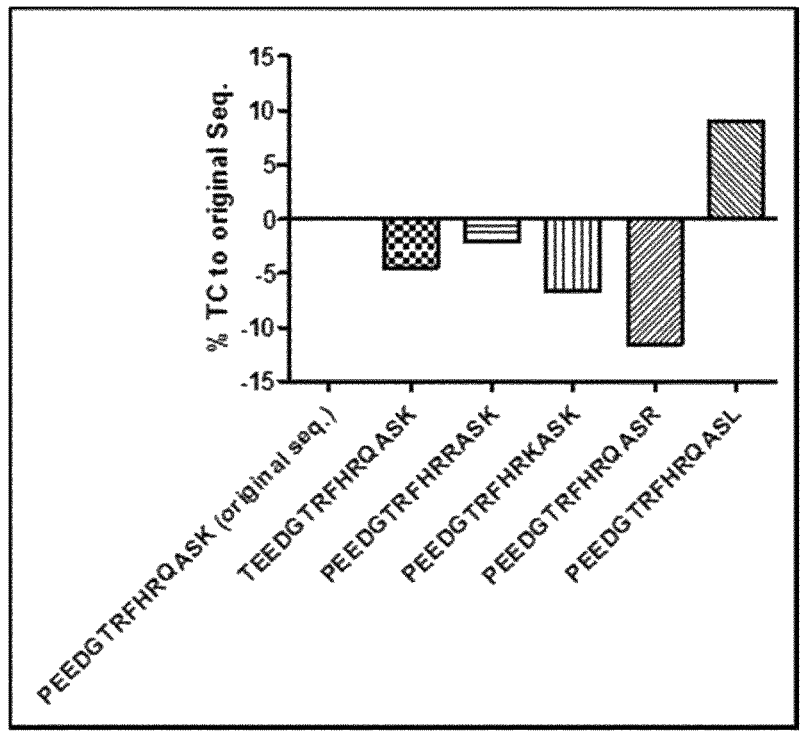
FIG. 5 shows % difference of TC of VARITOPE® treated groups in comparison to the group treated with the original sequence set to 0. Figure discloses SEQ ID NOS 1, 9, 17, 18, 23, and 24, respectively, in order of appearance.

Since the aim of this experiment was to compare VARIOTOPE® treated groups with the group treated with the original native sequence, in FIG. 5 the % reduction of TC values of vaccine treated groups compared to the group treated with the original sequence set to 0% is presented.

As depicted in FIG. 5 vaccines containing the sequences

| SEQ ID NO: 9: | TEEDGTREHRQASK |
|---|---|
| SEQ ID NO: 17: | PEEDGTRFHRRASK |
| SEQ ID NO: 18: | PEEDGTRFHRKASK |
| SEQ ID NO: 23: | PEEDGTRFHRQASR | are 3 to 10% more powerful to reduce TC levels in comparison to the vaccine containing the original sequence. In contrast to this, the vaccine containing the SEQ ID NO: 24: PEEDGTRFHRQASL possesses the ability to reduce TC levels compared to the negative control (FIG. 4) but compared to the original peptide containing vaccine the TC levels were higher (+9%).

In a further experiment following VARIOTOPE®s were tested and compared again to SEQ ID NO: 1:

| SEQ ID NO: 2: | AEEDGTRFHRQASK |
|---|---|
| SEQ ID NO: 10: | PQEDGTRFHRQASK |
| SEQ ID NO: 36: | PEEDGTRFHRTASK |

In this experiment 10 animals per group were injected five times in 2 week intervals with vaccines containing 1 μg of net peptide. Blood samples were taken again approximately 2 weeks after the final injection. In order to compare TC reduction in these animals directly with the TC values in animals treated with the original sequence % reduction of TC values of VARITOPE® vaccine treated groups compared to the group treated with the original sequence set to 0% is presented in FIG. 6.

Figure 6:
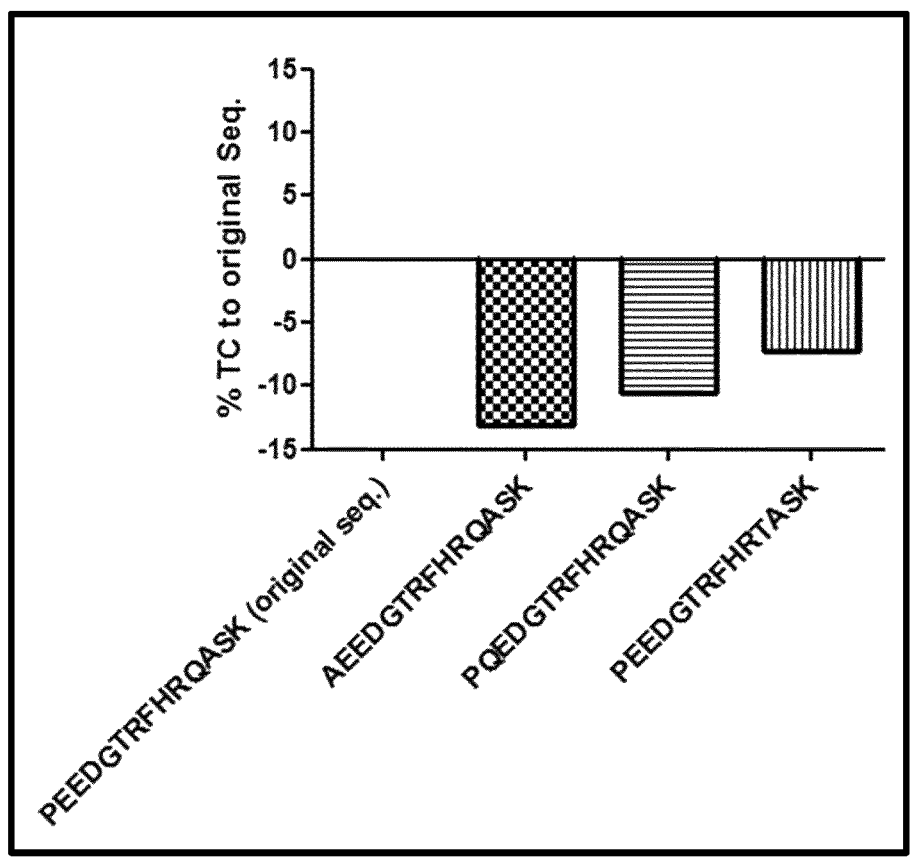
FIG. 6 shows % difference of TC of VARITOPE® treated groups in comparison to the group treated with the original sequence set to 0. Figure discloses SEQ ID NOS 1, 2, 10, and 36, respectively, in order of appearance.

As shown in FIG. 6 all three vaccine candidates tested in this experiment were more powerful in reducing TC levels compared to the vaccine containing the original sequence (−7% to −13%).

Based on the disclosure, the following preferred embodiments can be specifically highlighted:

1. Vaccine comprising at least one peptide consisting of 9 to amino acid residues, said peptide being a variant of the peptide PEEDGTRFHRQASK (SEQ ID NO: 1) with an increased immunogenicity in mammals, especially humans, compared to PEEDGTRFHRQASK (SEQ ID NO: 1) and wherein said variant is characterised by at least one and at most four amino acid exchanges compared to PEEDGTRFHRQASK (SEQ ID NO: 1), wherein said variant is preferably selected from the group consisting of AEEDGTRFHRQASK (SEQ ID NO: 2), TEEDGTRFHRQASK (SEQ ID NO: 9), PQEDGTRFHRQASK (SEQ ID NO: 10), PEEDGTRFHRRASK (SEQ ID NO: 17), PEEDGTRFHRKASK (SEQ ID NO: 18), PEEDGTRFHRQASR (SEQ ID NO: 23), and PEEDGTRFHRTASK (SEQ ID NO: 36).

2. Vaccine according to embodiment 1, comprising at least one peptide consisting of 9 to 25 amino acid residues, said peptide having or comprising the amino acid sequence $$X_1X_2EDGX_6RFX_9X_{10}X_{11}X_{12}X_{13}X_{14},$$ (SEQ ID NO: 46)

wherein
$X_1$ is an amino acid residue selected from the group consisting of lysine, threonine, alanine and proline, preferably alanine or proline,
$X_2$ is glutamine or aspartic acid, preferably aspartic acid,
$X_6$ is threonine or serine,
$X_9$ is an amino acid residue selected from the group consisting of histidine, alanine and serine,
$X_{10}$ is an amino acid residue selected from the group consisting of arginine, alanine, glutamine, lysine, methionine, proline and serine, preferably arginine, serine or alanine,
$X_{11}$ is an amino acid residue selected from the group consisting of glutamine, alanine, glutamic acid, lysine, threonine, and arginine, preferably glutamine, lysine, arginine, and threonine,
$X_{12}$ is an amino acid residue selected from the group consisting of alanine, serine and threonine, preferably alanine or serine,
$X_{13}$ is an amino acid residue selected from the group consisting of serine, alanine, and asparagine, preferably serine,
$X_{14}$ is an amino acid residue selected from the group consisting of lysine, alanine, arginine, leucine, serine, threonine, and valine, preferably lysine or serine,
or a fragment of SEQ ID NO: 46 having at least 9 consecutive amino acid residues, and
wherein SEQ ID NO: 46 is not PEEDGTRFHRQASK (SEQ ID NO: 1) or a N- or C-terminally truncated fragment thereof.

3. Vaccine according to embodiment 1 or 2, wherein the peptide consists or comprises an amino acid sequence selected from the group consisting of AEEDGTRFHRQASK (SEQ ID NO: 2), PEEDGTRFARQASK (SEQ ID NO: 4), PEEDGTRFHAQASK (SEQ ID NO: 5), PEEDGTRFHRAASK (SEQ ID NO: 6), PEEDGTRFHRQAAK (SEQ ID NO: 7), PEEDGTRFHRQASA (SEQ ID NO: 8), TEEDGTRFHRQASK (SEQ ID NO: 9), PQEDGTRFHRQASK (SEQ ID NO: 10), PEEDGSRFHRQASK (SEQ ID NO: 12), PEEDGTRFHQQASK (SEQ ID NO: 13), PEEDGTRFHKQASK (SEQ ID NO: 14), PEEDGTRFHMQASK (SEQ ID NO: 15), PEEDGTRFHREASK (SEQ ID NO: 16), PEEDGTRFHRRASK (SEQ ID NO: 17), PEEDGTRFHRKASK (SEQ ID NO: 18), PEEDGTRFHRQSSK (SEQ ID NO: 19), PEEDGTRFHRQANK (SEQ ID NO: 21), PEEDGTRFHRQASR (SEQ ID NO: 23), PEEDGTRFHRQASL (SEQ ID NO: 24), KEEDGTRFHRQASK (SEQ ID NO: 25), PEEDGTRFSRQASK (SEQ ID NO: 29), PEEDGTRFMRQASK (SEQ ID NO: 33), PEEDGTRFHPQASK (SEQ ID NO: 34), PEEDGTRFHSQASK (SEQ ID NO: 35), PEEDGTRFHRTASK (SEQ ID NO: 36), PEEDGTRFHRQTSK (SEQ ID NO: 37), PEEDGTRFHRQASS (SEQ ID NO: 38), PEEDGTRFHRQAST (SEQ ID NO: 39), PEEDGTRFHRQASV (SEQ ID NO: 40), PEEDGSRFHKQASK (SEQ ID NO: 41), PEEDGSRFHMQASK (SEQ ID NO: 42), PEEDGSRFHRRASK (SEQ ID NO: 43), and PEEDGSRFHRQATK (SEQ ID NO: 44); preferably AEEDGTRFHRQASK (SEQ ID NO: 2), PEEDGTRFARQASK (SEQ ID NO: 4), PEEDGTRFHAQASK (SEQ ID NO: 5), PEEDGTRFHRAASK (SEQ ID NO: 6), PEEDGTRFHRQASA (SEQ ID NO: 8), TEEDGTRFHRQASK (SEQ ID NO: 9), PQEDGTRFHRQASK (SEQ ID NO: 10), PEEDGTRFHRRASK (SEQ ID NO: 17), PEEDGTRFHRKASK (SEQ ID NO: 18), PEEDGTRFHRQSSK (SEQ ID NO: 19), PEEDGTRFSRQASK (SEQ ID NO: 29), PEEDGTRFHPQASK (SEQ ID NO: 34), PEEDGTRFHSQASK (SEQ ID NO: 35), PEEDGTRFHRTASK (SEQ ID NO: 36), PEEDGTRFHRQTSK (SEQ ID NO: 37), PEED- GTRFHRQASS (SEQ ID NO: 38), PEEDGTRFHRQASV (SEQ ID NO: 40), PEEDGSRFHKQASK (SEQ ID NO: 41), PEEDGSRFHRRASK (SEQ ID NO: 43), and PEEDGSR-FHRQATK (SEQ ID NO: 44); especially AEEDGTRF-HRQASK (SEQ ID NO: 2), PEEDGTRFHAQASK (SEQ ID NO: 5), PQEDGTRFHRQASK (SEQ ID NO: 10), PEEDGTRFHRRASK (SEQ ID NO: 17), PEEDGTRF-HRRASK (SEQ ID NO: 18), PEEDGTRFHRQSSK (SEQ ID NO: 19), PEEDGTRFSRQASK (SEQ ID NO: 29), PEEDGTRFHSQASK (SEQ ID NO: 35), PEEDGTRF-HRTASK (SEQ ID NO: 36), PEEDGTRFHRQTSK (SEQ ID NO: 37), PEEDGTRFHRQASS (SEQ ID NO: 38), PEEDGSRFHKQASK (SEQ ID NO: 41) and PEEDGSRF-HRRASK (SEQ ID NO: 43).

4. Vaccine according to any one of embodiments 1 to 3, wherein said at least one peptide is coupled or fused to a pharmaceutically acceptable carrier.

5. Vaccine according to any one of embodiments 1 to 4, wherein the at least one peptide comprises at its N- and/or C-terminus at least one cysteine residue bound directly or via a spacer sequence thereto.

6. Vaccine according to embodiment 4 or 5, wherein the pharmaceutically acceptable carrier is a protein carrier.

7. Vaccine according to embodiment 6, wherein the protein carrier is selected from the group consisting of keyhole limpet haemocyanin (KLH), tetanus toxoid (TT), CRM197, protein D or a diphtheria toxin (DT), preferably a mutated diphtheria toxin, CRM197, or KLH, especially KLH.

8. Vaccine according to any one of embodiments 1 to 7, wherein the vaccine is formulated with an adjuvant, preferably with Al(OH)$_3$ (Alhydrogel).

9. Vaccine according to any one of embodiments 1 to 8, wherein said at least one peptide consists of 9 to 20 amino acid residues, especially 9 to 15 amino acid residues.

10. Vaccine according to any one of embodiments 1 to 9, wherein said at least one peptide consists of 10, 11, 12, 13, 14 or 15 amino acid residues, preferably 13 or 14 amino acid residues, especially 14 amino acid residues.

11. Vaccine according to any one of embodiments 1 to 10, comprising at least 2, at least 3, or at least 4 of said peptides consisting of 9 to 25 amino acid residues.

12. Vaccine according to any one of embodiments 1 to 11, comprising the at least one peptide in an amount of 0.1 ng to 10 mg, preferably of 0.5 to 500 µg, more preferably 1 to 100 µg.

13. Vaccine according to any one of embodiments 1 to 12, wherein the peptide has an increased immunogenicity, compared to the peptide PEEDGTRFHRQASK (SEQ ID NO: 1), of at least 50%, preferably at least 100%, especially at least 200%, as evidenced in a serum ELISA.

14. Vaccine according to any one of embodiments 1 to 13, wherein the peptide has an increased ability to reduce total cholesterol levels, compared to the peptide PEEDGTRF-HRQASK (SEQ ID NO: 1), of at least 3%, preferably at least 5%, especially at least 10%, as evidenced in a serum cholesterol test.

15. Vaccine according to any one of embodiments 1 to 14 for use in a method for treating and/or preventing disorders caused by hyperlipidemia, hypercholesterolemia and/or atherosclerosis, preferably cardiovascular diseases, stroke or peripheral vascular diseases, or neoplastic diseases, preferably melanoma and liver cancer metastasis linked to PCSK9.

16. Peptide consisting of 9 to 25 amino acid residues, said peptide being a variant of the peptide PEEDGTRFHRQASK (SEQ ID NO: 1) with an increased immunogenicity in mammals, especially humans, compared to PEEDGTRF-HRQASK (SEQ ID NO: 1) and wherein said variant is characterised by at least one and at most four amino acid exchanges compared to PEEDGTRFHRQASK (SEQ ID NO: 1).

17. Peptide according to embodiment 16, consisting of 9 to 25 amino acid residues, said peptide having or comprising the amino acid sequence (SEQ ID NO: 46)
$X_1X_2EDGX_6RFX_9X_{10}X_{11}X_{12}X_{13}X_{14}$, wherein $X_1$ is an amino acid residue selected from the group consisting of lysine, threonine, alanine and proline, preferably alanine or proline, $X_2$ is glutamine or aspartic acid, preferably aspartic acid, $X_6$ is threonine or serine, $X_9$ is an amino acid residue selected from the group consisting of histidine, alanine and serine $X_{10}$ is an amino acid residue selected from the group consisting of arginine, alanine, glutamine, lysine, methionine, proline and serine, preferably arginine, serine or alanine, $X_{11}$ is an amino acid residue selected from the group consisting of glutamine, alanine, glutamic acid, lysine, threonine, and arginine, preferably glutamine, lysine, arginine, and threonine, $X_{12}$ is an amino acid residue selected from the group consisting of alanine, serine and threonine, preferably alanine or serine, $X_{13}$ is an amino acid residue selected from the group consisting of serine, alanine, and asparagine, preferably serine, $X_{14}$ is an amino acid residue selected from the group consisting of lysine, alanine, arginine, leucine, serine, threonine, and valine, preferably lysine or serine, or a fragment of SEQ ID NO: 46 having at least 9 consecutive amino acid residues, and wherein SEQ ID NO: 46 is not PEEDGTRFHRQASK (SEQ ID NO: 1) or a N- or C-terminally truncated fragment thereof.

18. Peptide according to embodiment 16 or 17, wherein the peptide consists or comprises an amino acid sequence selected from the group consisting of AEEDGTRF-HRQASK (SEQ ID NO: 2), PEEDGTRFARQASK (SEQ ID NO: 4), PEEDGTRFHAQASK (SEQ ID NO: 5), PEEDG-TRFHRAASK (SEQ ID NO: 6), PEEDGTRFHRQAAK (SEQ ID NO: 7), PEEDGTRFHRQASA (SEQ ID NO: 8), TEEDGTRFHRQASK (SEQ ID NO: 9), PQEDGTRF-HRQASK (SEQ ID NO: 10), PEEDGSRFHRQASK (SEQ ID NO: 12), PEEDGTRFHQQASK (SEQ ID NO: 13), PEEDGTRFHKQASK (SEQ ID NO: 14), PEEDGTRFH-MQASK (SEQ ID NO: 15), PEEDGTRFHREASK (SEQ ID NO: 16), PEEDGTRFHRRASK (SEQ ID NO: 17), PEED-GTRFHRKASK (SEQ ID NO: 18), PEEDGTRFHRQSSK (SEQ ID NO: 19), PEEDGTRFHRQANK (SEQ ID NO: 21), PEEDGTRFHRQASR (SEQ ID NO: 23), PEEDGTRF-HRQASL (SEQ ID NO: 24), KEEDGTRFHRQASK (SEQ ID NO: 25), PEEDGTRFSRQASK (SEQ ID NO: 29), PEEDGTRFMRQASK (SEQ ID NO: 33), PEEDGTRFH-PQASK (SEQ ID NO: 34), PEEDGTRFHSQASK (SEQ ID NO: 35), PEEDGTRFHRTASK (SEQ ID NO: 36), PEED-GTRFHRQTSK (SEQ ID NO: 37), PEEDGTRFHRQASS (SEQ ID NO: 38), PEEDGTRFHRQAST (SEQ ID NO: 39), PEEDGTRFHRQASV (SEQ ID NO: 40), PEEDGSRFH-KQASK (SEQ ID NO: 41), PEEDGSRFHMQASK (SEQ ID NO: 42), PEEDGSRFHRRASK (SEQ ID NO: 43), and PEEDGSRFHRQATK (SEQ ID NO: 44); preferably AEEDGTRFHRQASK (SEQ ID NO: 2), PEEDGTRFAR-QASK (SEQ ID NO: 4), PEEDGTRFHAQASK (SEQ ID NO: 5), PEEDGTRFHREASK (SEQ ID NO: 6), PEEDG-TRFHRQASA (SEQ ID NO: 8), TEEDGTRFHRQASK (SEQ ID NO: 9), PQEDGTRFHRQASK (SEQ ID NO: 10), PEEDGTRFHRRASK (SEQ ID NO: 17), PEEDGTRF-HRKASK (SEQ ID NO: 18), PEEDGTRFHRQSSK (SEQ ID NO: 19), PEEDGTRFSRQASK (SEQ ID NO: 29), PEEDGTRFHPQASK (SEQ ID NO: 34), PEEDGTRFH-SQASK (SEQ ID NO: 35), PEEDGTRFHRTASK (SEQ ID NO: 36), PEEDGTRFHRQTSK (SEQ ID NO: 37), PEED-GTRFHRQASS (SEQ ID NO: 38), PEEDGTRFHRQASV (SEQ ID NO: 40), PEEDGSRFHKQASK (SEQ ID NO: 41), PEEDGSRFHRRASK (SEQ ID NO: 43), and PEEDGSR-FHRQATK (SEQ ID NO: 44); especially AEEDGTRF-HRQASK (SEQ ID NO: 2), PEEDGTRFHAQASK (SEQ ID NO: 5), PQEDGTRFHRQASK (SEQ ID NO: 10), PEEDGTRFHRRASK (SEQ ID NO: 17), PEEDGTRF-HRKASK (SEQ ID NO: 18), PEEDGTRFHRQSSK (SEQ ID NO: 19), PEEDGTRFSRQASK (SEQ ID NO: 29), PEEDGTRFHSQASK (SEQ ID NO: 35), PEEDGTRF-HRTASK (SEQ ID NO: 36), PEEDGTRFHRQTSK (SEQ ID NO: 37), PEEDGTRFHRQASS (SEQ ID NO: 38), PEEDGSRFHKQASK (SEQ ID NO: 41) and PEEDGSRF-HRRASK (SEQ ID NO: 43).

19. Peptide according to any one of embodiments 16 to 18, wherein the peptide consists of 9 to 20 amino acid residues, especially 9 to 15 amino acid residues.

20. Peptide according to any one of embodiments 16 to 19, wherein the peptide consists of 10, 11, 12, 13, 14 or 15 amino acid residues, preferably 13 or 14 amino acid residues, especially 14 amino acid residues.

21. Peptide according to any one of embodiments 16 to 20, wherein the peptide has an increased immunogenicity, compared to the peptide PEEDGTRFHRQASK (SEQ ID NO: 1), of at least 50%, preferably at least 100%, especially at least 200%, as evidenced in a serum ELISA.

22. Peptide according to any one of embodiments 16 to 21, wherein the peptide has an increased ability to reduce total cholesterol levels, compared to the peptide PEEDGTRF-HRQASK (SEQ ID NO: 1), of at least 3%, preferably at least 5%, especially at least 10%, as evidenced in a serum cholesterol test.

23. Method for treatment of patients having or having a risk of developing disorders caused by hyperlipidemia, hypercholesterolemia and/or atherosclerosis, comprising administering to the patient an effective amount of a vaccine according to any one of embodiments 1 to 15.

24. Method according to embodiment 23, wherein the disorder is selected from the group consisting of cardiovascular diseases, stroke or peripheral vascular diseases.

25. Method according to embodiment 23 or 24, wherein preferably subcutaneously, intramuscularly, intradermally, or intravenously.

26. Method according to any one of embodiments 23 to 25, wherein the vaccine administered contains the at least one peptide in an amount of 0.1 ng to 10 mg, preferably of 0.5 to 500 μg, especially 1 to 100 μg.

27. Method according to any one of embodiments 23 to 26, wherein the vaccine is applied between 2 and 10, preferably between 2 and 7, and most preferably up to 5 times to the patient.

28. Method according to any one of embodiments 23 to 27, wherein the vaccine is administered at least twice and wherein the interval of administration is between 2 weeks and 5 years, preferably between 1 month and up to 3 years, more preferably between 2 months and 1.5 years.

29. Method according to any one of embodiments 23 to 28, wherein the vaccine is administered for 3 to 4 initial vaccinations over a period of 6 to 8 weeks and up to 6 months, preferably followed with further administrations after such initial vaccinations.

SUMMARY

The present invention relates to a vaccine capable to induce production of antibodies directed to PCSK9 in vivo.

---

The invention claimed is:

1. A vaccine comprising at least one peptide selected from the group consisting of PEEDGTRFHRTASK (SEQ ID NO: 17), PEEDGTRFHRKASK (SEQ ID NO: 18), PEEDGTRFHRTASK (SEQ ID NO: 36), PEEDGSRFHKQASK (SEQ ID NO: 41), and PEEDGSRFHRQATK (SEQ ID NO: 44).

2. The vaccine according to claim 1, wherein said at least one peptide is coupled or fused to a pharmaceutically acceptable carrier.

3. The vaccine according to claim 1, wherein the at least one peptide further comprises at its N- and/or C-terminus at least one cysteine residue bound directly or via a spacer sequence thereto.

4. The vaccine according to claim 2, wherein the pharmaceutically acceptable carrier is a protein carrier.

5. The vaccine according to claim 4, wherein the protein carrier is at least one selected from the group consisting of keyhole limpet haemocyanin (KLH), tetanus toxoid (TT), CRM197, protein D, a diphtheria toxin (DT) and a mutated diphtheria toxin.

6. The vaccine according to claim 1, further comprising Al(OH)$_3$ or another adjuvant.

7. A method for treating and/or preventing a disorder caused by hyperlipidemia, hypercholesterolemia and/or atherosclerosis, a cardiovascular disease, stroke, a peripheral vascular disease, a neoplastic disease, melanoma or liver cancer metastasis linked to PCSK9 comprising administering the vaccine according to claim 1 to a subject in need thereof.

8. A peptide having an amino acid sequence selected from the group consisting of PEEDGTRFHRRASK (SEQ ID NO:17), PEEDGTRFHRKASK (SEQ ID NO:18), PEEDGTRFHRTASK (SEQ ID NO:36), PEEDGSRFHKQASK (SEQ ID NO:41), and PEEDGSRFHRQATK (SEQ ID NO:44).

9. A method for treating a subject having or having a risk of developing a disorder caused by hyperlipidemia, hypercholesterolemia and/or atherosclerosis comprising administering the peptide according to claim 8 to said subject.

10. The method of claim 9, wherein said subject has hyperlipidemia, hypercholesterolemia and/or atherosclerosis.

11. A method for inducing an antibody that neutralizes PCSK9 comprising administering the peptide according to claim 8 to a subject in need thereof.

12. A method for inhibiting PCSK-mediated degradation of LDLR or for reducing plasma LDL cholesterol level comprising administering the peptide according to claim 8 to a subject in need thereof.

13. The vaccine according to claim 1 comprising the peptide of PEEDGTRFHRRASK (SEQ ID NO: 17).

14. The vaccine according to claim 1 comprising the peptide of PEEDGTRFHRKASK (SEQ ID NO: 18).

15. The vaccine according to claim 1 comprising the peptide of PEEDGTRFHRTASK (SEQ ID NO: 36).

16. The vaccine according to claim 1 comprising the peptide of PEEDGSRFHKQASK (SEQ ID NO: 41).

17. The vaccine according to claim 1 comprising the peptide of PEEDGSRFHRQATK (SEQ ID NO: 44).

* * * * *